US012780785B2

(12) United States Patent
Okada et al.

(10) Patent No.: US 12,780,785 B2
(45) Date of Patent: Nov. 3, 2026

(54) AZABICYCLO[3.1.0]HEXANE COMPOUND

(71) Applicant: OTSUKA PHARMACEUTICAL CO., LTD., Tokyo (JP)

(72) Inventors: Minoru Okada, Osaka (JP); Nobuaki Ito, Osaka (JP); Masakazu Shibata, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 358 days.

(21) Appl. No.: 18/569,850

(22) PCT Filed: Jun. 14, 2022

(86) PCT No.: PCT/JP2022/023841

§ 371 (c)(1),
(2) Date: Dec. 13, 2023

(87) PCT Pub. No.: WO2022/265020

PCT Pub. Date: Dec. 22, 2022

(65) Prior Publication Data

US 2024/0286999 A1 Aug. 29, 2024

(30) Foreign Application Priority Data

Jun. 15, 2021 (JP) ................................ 2021-099630

(51) Int. Cl.

| | |
|---|---|
| ***C07D 209/52*** | (2006.01) |
| ***A61K 31/403*** | (2006.01) |
| ***A61K 31/4439*** | (2006.01) |
| ***A61K 31/675*** | (2006.01) |
| ***C07D 401/06*** | (2006.01) |
| ***C07F 9/572*** | (2006.01) |
| ***C07F 9/58*** | (2006.01) |
| ***C07F 9/6558*** | (2006.01) |

(52) U.S. Cl.

CPC .......... *C07D 209/52* (2013.01); *A61K 31/403* (2013.01); *A61K 31/4439* (2013.01); *A61K 31/675* (2013.01); *C07D 401/06* (2013.01); *C07F 9/5728* (2013.01); *C07F 9/58* (2013.01); *C07F 9/65583* (2013.01)

(58) Field of Classification Search

None

See application file for complete search history.

(56) References Cited

U.S. PATENT DOCUMENTS 7,067,507 B2 * 6/2006 Pulley ...................... A61P 9/00 514/183
2021/0087186 A1 3/2021 Tanaka et al.

FOREIGN PATENT DOCUMENTS

| | | | |
|---|---|---|---|
| JP | 2009-502939 | A | 1/2009 |
| JP | 2009-502941 | A | 1/2009 |
| JP | 2012-531403 | A | 12/2012 |
| JP | 5184354 | B2 | 4/2013 |
| WO | 2007/014264 | A2 | 2/2007 |
| WO | 2007/016155 | A2 | 2/2007 |
| WO | 2010/150281 | A2 | 12/2010 |

OTHER PUBLICATIONS

International Search Report of PCT/JP2022/023841 dated Aug. 30, 2022 [PCT/ISA/210].

Extended European Search Report dated Oct. 29, 2025 in European Application No. 22825008.0.

Ana L. Simplício, et al., "Prodrugs for Amines", Molecules, 2008, vol. 13, No. 3, pp. 519-547, (29 pages).

International Preliminary Report on Patentability (with translation of Written Opinion) dated Dec. 28, 2023 in International Application No. PCT/JP2022/023841.

* cited by examiner

*Primary Examiner* — Noble E Jarrell

(74) *Attorney, Agent, or Firm* — Fish & Richardson P.C.

(57) ABSTRACT

The present invention provides a new azabicyclo[3.1.0]hexane compound that is represented by the following formula:

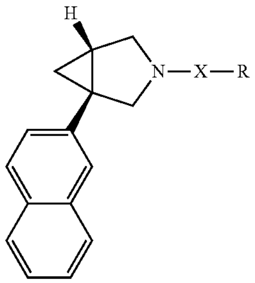

and that is for use in treating central nervous system (CNS) disorders. In the formula, X represents —C(=)—O— or the like, and R represents H, an optionally substituted $C_1$-$C_{18}$ alkyl, or the like.

8 Claims, No Drawings

AZABICYCLO[3.1.0]HEXANE COMPOUND

CROSS REFERENCE TO RELATED APPLICATIONS

This application is a National Stage of International Application No. PCT/JP2022/023841 filed on Jun. 14, 2022, claiming priority based on Japanese Patent Application No. 2021-099630 filed on Jun. 15, 2021.

TECHNICAL FIELD

The present invention relates to novel azabicyclo[3.1.0] hexane compounds and salts thereof, and their use in the treatment of central nervous system (CNS) disorders.

BACKGROUND ART (1R,5S)-1-(naphthalen-2-yl)-3-azabicyclo[3.1.0]hexane, also known as (+)-1-(naphthalen-2-yl)-3-azabicyclo[3.1.0] hexane, inhibits the reuptake of three biogenic amines of norepinephrine, serotonin, and dopamine (Patent Literature 1).

(1R,5S)-1-(naphthalen-2-yl)-3-azabicyclo[3.1.0]hexane is most effective against norepinephrine reuptake (NE), one-sixth as effective against dopamine reuptake (DA), and one-fourteenth as effective against serotonin reuptake (5-HT), and thus is useful as an unbalanced triple reuptake inhibitor (TRI). Based on these effects, the compound is useful as a medicament for treating CNS disorders such as depression, anxiety, and attention deficit hyperactivity disorder (ADHD).

One approach to drug design in the field of pharmaceuticals is to chemically transform or modify some functional groups of known drug molecules to improve their efficacy and slow their metabolism in vivo. These newly designed compounds may exhibit characteristics such as being more stable or being released for a longer time in the patient's body than the known drugs, thereby resulting in sustained drug effects.

The discovery of novel azabicyclo[3.1.0]hexane compounds and the provision of new options to medicaments for various CNS disorders are much desired by patients suffering from such disorders.

CITATION LIST

Patent Literature

[Patent Literature 1] JP 5184354 B

SUMMARY OF INVENTION

Technical Problem

One of the problems to be solved by the present invention is to provide a new medicament for treating CNS disorders.

Solution to Problem

As a result of intensive research, the inventors have succeeded in developing a new azabicyclo[3.1.0]hexane compound, which is shown in the following formula [I], and a salt thereof, and found that they can be new medicaments for CNS disorders. The present invention has been completed based on these findings.

One embodiment of the present invention is a novel azabicyclo[3.1.0]hexane compound represented by the following Formula [I]:

[Chemical formula 1]

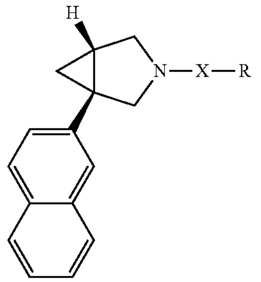

wherein

X is

1) —C(═O)—O—,

2) —C(═O)—O—C($X^{11a}$)($X^{12a}$)—O—C(═O)—,

3) —C(═O)—O—C($X^{11b}$)($X^{12b}$)—O—P(═O)(—O$R^{2b}$)—O—

4) —C(═O)—,

5) —C(═O)—C($X^{11c}$)($X^{12c}$)—N($X^{13c}$)—C(═O)—,

6) —C($X^{11d}$)($X^{12d}$)—O—C(═O)—,

7) ═C($X^{11e}$)($X^{12e}$)—N($X^{13e}$)—C(═O)—,

8) ~C($X^{11f}$($X^{12f}$)—O—P(═O)(—O$R^{2f}$)—O—,

9) —C($X^{11g}$($X^{12g}$)—O—P(═O)(—O$R^{2g}$)—O═C($X^{11h}$)($X^{12h}$)—O—C(═O)—, or

10) —P(═O)(—O$R^{2i}$)—O—;

$X^{11a}$, $X^{11b}$, $X^{11c}$, $X^{11d}$, $X^{11e}$, $X^{11f}$, $X^{11g}$, $X^{11h}$, $X^{12a}$, $X^{12b}$, $X^{12c}$, $X^{12d}$, $X^{12e}$, $X^{12f}$, $X^{12g}$, and $X^{12h}$ are independently H or an optionally substituted $C_1$-$C_6$ alkyl, or $X^{11a}$ and $X^{12a}$, $X^{11b}$ and $X^{12b}$, $X^{11c}$ and $X^{12c}$, $X^{11d}$ and $X^{12d}$, $X^{11e}$ and $X^{12e}$, $X^{11f}$ and $X^{12f}$, $X^{11g}$ and $X^{12g}$, and $X^{11b}$ and $X^{12h}$ each may be taken together with a carbon atom to which they are both bonded to form a $C_3$-$C_6$ cycloalkane ring or a 3- to 6-membered heterocycloalkane ring;

$X^{13c}$ and $x^{13e}$ are Independently H or an optionally substituted $C_1$-$C_6$ alkyl;

R, $R^{2b}$, $R^{2f}$, $R^{2g}$ and $R^{2f}$ are independently i) H, ii) an optionally substituted $C_1$-$C_{18}$ alkyl, iii) an optionally substituted $C_2$-$C_{18}$ alkenyl, iv) an optionally substituted $C_2$-$C_{18}$ alkynyl, v) an optionally substituted 3- to 15-membered hydrocarbon ring group, or vi) an optionally substituted 3- to 15-membered heterocyclic ring group, or a salt thereof (also referred to herein as "compound of Formula [I]").

Effect of the Invention

The compound of Formula [I] is a compound in which the nitrogen atom at position 3 of (1R,5S)-1-(naphthalen-2-yl)-3-azabicyclo[3.1.0]hexane is chemically modified appropriately, and thus can provide a prolonged metabolic half-life, mainly in the intestine and liver and can improve bioavailability, compared to when (1R,5S)-1-(naphthalen-2-yl)-3-azabicyclo[3.1.0]hexane is administered to the body. Administration of the compound of Formula [I] may also enhance the persistence of its medicinal effect. The prolonged metabolic half-life may also lead to a reduction in the number of clinical doses and clinical doses administered to patients, which may improve patient compliance.

DESCRIPTION OF EMBODIMENTS

The words and terms used in the present description will be described in detail below.

The "alkyl" includes, for example, a linear or branched alkyl having 1 to 18 carbon atoms $C_1$-$C_{18}$ alkyl) such as $C_1$-$C_{14}$ alkyl, and specific examples thereof include methyl, ethyl, propyl, isopropyl, butyl, isobutyl, sec-butyl, tert-butyl, pentyl, isopentyl, neopentyl, hexyl, isohexyl, 3-methylpentyl, heptyl, octyl, nonyl, decyl, tetradecyl, etc.

The "alkenyl" includes, for example, a linear or branched alkenyl having 2 to 18 carbon atoms and 1 to 3 double bonds ($C_2$-$C_{18}$ alkenyl), preferably $C_2$-$C_6$ alkenyl, and specific examples thereof include vinyl (ethenyl), 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pantenyl, 1-hexenyl, 3-hexenyl, 5-hexenyl, etc.

The "alkynyl" includes, for example, a linear or branched alkynyl having 2 to 18 carbon atoms and 1 to 3 triple bonds ($C_2$-$C_{18}$ alkynyl), preferably $C_2$-$C_6$ alkynyl, and specific examples thereof include 1-propynyl, 2-propynyl, 1-butynyl, 2-butynyl, 3-butynyl, 1-pentynyl, 2-pentynyl, 3-pentynyl, 4-pentynyl, 4-methyl-2-pentynyl, 1-hexynyl, 2-hexynyl, 3-hexynyl, 4-hexynyl, 5-hexynyl, etc.

The "alkoxy" includes, for example, a linear or branched alkoxy having 1 to 6 carbon atoms ($C_1$-$C_6$ alkoxy), and specific examples thereof include methoxy, ethoxy, propoxy, isopropoxy, butoxy, isobutoxy, sec-butoxy, tert-butoxy, pentyloxy, isopentylozy, neopentyloxy, hexyloxy, isohexyloxy, and 3-methylpentyloxy, etc.

The "hydroxy alkyl" refers to the above "alkyl" substituted by a hydroxyl group, for example, hydroxy $C_1$-$C_{18}$ alkyl, hydroxy $C_1$-$C_{14}$ alkyl, hydroxy $C_1$-$C_{10}$ alkyl, hydroxy $C_1$-$C_8$ alkyl, hydroxy $C_1$-$C_6$ alkyl, hydroxy $C_1$-$C_4$ alkyl, and specific examples thereof include hydroxymethyl, hydroxyethyl, hydroxypropyl, etc.

Examples of "cycloalkyl" include a cyclic alkyl having 3 to 6 carbon atoms ($C_3$-$C_6$ cycloalkyl), specifically cyclopropyl, cyclobutyl, cyclopentyl, cyclohexyl, etc.

Examples of "cycloalkenyl" include a cyclic alkenyl having 3 to 6 carbon atoms and 1 to 3 double bonds ($C_3$-$C_6$ cycloalkenyl), specifically 2-cyclopentenyl, 3-cyclopentenyl, 2-cyclohexenyl, 3-cyclohexenyl, etc.

Examples of "cycloalkoxy" include a cyclic alkoxy having 3 to 6 carbon atoms ($C_3$-$C_6$ cycloalkoxy), specifically cyclopropyloxy, cyclobutyloxy, cyclopentyloxy, cyclohexyloxy, etc.

Examples of "cycloalkane" or "cycloalkane ring" include a saturated monocyclic hydrocarbon ring having 3 to 6 carbon atoms, specifically cyclopropane, cyclobutane, cyclopentane, cyclohexane, etc.

Examples of "heterocycloalkane" or "heterocycloalkane ring" include a 3- to 6-membered saturated monocyclic ring containing carbon atoms and 1 to 5 heteroatoms independently selected from the group consisting of nitrogen, oxygen, and sulfur. Specific examples thereof include aziridine, oxirane, thiirane, azetidine, oxetane, thietane, azolidine, oxolane, thiolane, azinane, oxane, thiane, dioxolane, dioxane, morpholine, etc.

The "alkanoyl" or "acyl" refers to any of the above groups such as "alkyl", "alkonyl", "alkynyl", or "cycloalkyl" attached to a carbonyl group, for example, R'—C(═O)— (wherein R' represents any group). Specific examples thereof include acetyl, propionyl, acryloyl, cyclohexanecarbonyl, etc.

The "alkanoyloxy" or "acyloxy" refers to the above "alkanoyl" or "acyl" group to which an oxygen atom is bonded, for example, R'—C(═O)—O— (wherein R' represents any group). Specific examples thereof include $C_1$-$C_6$ alkyl-C(═O)—O—, etc.

Examples of "aryl" include a monocyclic, bicyclic or tricyclic aromatic hydrocarbon having 6 to 14 carbon atoms ($C_6$-$C_{14}$ aryl), preferably $C_6$-$C_{10}$ aryl, specifically phenyl, naphthyl, anthryl, phenanthryl, etc.

Examples of "aralkyl" include a linear or branched alkyl having 1 to 3 carbon atoms substituted with monocyclic, bicyclic or tricyclic aromatic hydrocarbon groups having 6 to 14 carbon atoms ($C_7$-$C_{17}$ aralkyl), preferably $C_7$-$C_{12}$ aralkyl, specifically benzyl, 1-phenylethyl, 2-phenylethyl, 1-naphthylmethyl, 2-naphthylmethyl, etc.

Examples of "hydrocarbon ring" include a saturated or unsaturated monocyclic or polycyclic hydrocarbon ring, for example, a saturated or unsaturated 3- to 15-membered hydrocarbon ring, preferably a 3- to 14-membered saturated hydrocarbon ring or a 6- to 14-membered unsaturated hydrocarbon ring. More preferred is 6- to 10-membered monocyclic, bicyclic or tricyclic unsaturated hydrocarbon ring; or 3- to 10-membered monocyclic, bicyclic or tricyclic saturated hydrocarbon ring. An "unsaturated" ring refers to an aromatic ring, or an aromatic ring wherein the bonds between ring atoms are partially hydrogenated. The ring atoms of the hydrocarbon ring may be substituted with oxo to form an oxide. Specific examples of "hydrocarbon ring" include:

(a) a saturated or unsaturated 3- to 8-membered, preferably 5- or 6-membered, more preferably 6-membered monocyclic hydrocarbon ring; specifically, cyclopropane, cyclobutane, cyclopentane, cyclohexane, cycloheptane, cyclooctane, cyclobutene, cyclopentene, cyclohexene, cycloheptene, cyclooctene, benzene, etc.;

(b) a saturated or unsaturated 7- to 15-membered bicyclic or tricyclic hydrocarbon ring, preferably a saturated or unsaturated 7- to 14-membered, more preferably 7- to 10-membered bicyclic hydrocarbon ring; specifically, indene, dihydroindene, naphthalene, dihydronaphthalene, tetrahydronaphthalene, decahydronaphthalene, anthracene, phenanthrene, etc.; and the like.

Examples of "heterocyclic ring" include a saturated or unsaturated monocyclic or polycyclic heterocyclic ring containing 1 to 5 heteroatoms independently selected from the group consisting of nitrogen, oxygen and sulfur as ring constituent atoms, for example, a saturated or unsaturated 3- to 15-membered, preferably 5- to 10-membered monocyclic, bicyclic or tricyclic heterocyclic ring. An "unsaturated" ring refers to an aromatic ring, or an aromatic ring wherein the bonds between ring atoms ate partially hydrogenated. The "nitrogen-containing heterocyclic ring" refer to a heterocyclic ring containing at least one nitrogen atom as a ring constituent atom. The ring atoms of the heterocyclic ring may be substituted with oxo to form an oxide or dioxide, Specific examples of "heterocyclic ring" include:

(a) a saturated or unsaturated 3- to 8-membered, preferably 3- to 6-membered, more preferably 5- or 6-membered monocyclic heterocyclic ring containing 1 to 4 nitrogen atoms as ring constituent atoms; specifically, pyrrole, imidazole, pyrazole, pyridine, dihydropyridine, tetrahydropyridine, pyrimidine, pyrazine, pyridazine, triazole, tetrazole, dihydrotriazine, azetidine, pyrrolidine, imidazolidine, piperidine, pyrazolidine, piperazine, azepine, 1,4-diazepine, etc.;

(b) a saturated or unsaturated 7- to 15-membered bicyclic or tricyclic heterocyclic ring containing 1 to 5 nitrogen atoms as ring constituent atoms, preferably a saturated or unsaturated 7- to 12-membered, more preferably a 7- to 10-membered bicyclic or tricyclic heterocyclic ring containing 1 to 3 nitrogen atoms as ring constituent atoms; specifically, indole, indoline (dihydroindole), isoindole, isoindoline (dihydroisoindole), benzoimidazole, dihydrobenzoimidazole, indazole, indazoline (dihydroindazole), quinoline, dihydroquinoline, tetrahydroquinoline, decahydroquinoline, isoquinoline, dihydroisoquinoline, tetrahydroisoquinoline, benzotriazole, tetrazolopyridine, tetrazolopyridazine, dihydrotriazolopyridazine, imidazopyridine, naphthyridine, tetrahydronaphthyridine, hexahydronaphthyridine, synthrin, quinoline, dihydroquinoxaline, tetrahydroquinoxaline, quinazoline, dihydroquinazoline, tetrahydroquinazoline, pyrazolopyridine, tetrahydropyridindole, benzoazepine, tetrahydrobenzoazepine, carbazole, phenanthridine, dihydrophenanthridine, etc.;

(c) a saturated or unsaturated 3- to 8-membered (preferably 5- or 6-membered) monocyclic heterocyclic ring containing 1 or 2 oxygen atoms as ring constituent atoms; specifically, furan, tetrabydropyran, tetrahydrofuran, dioxane, etc.;

(d) a saturated or unsaturated 7- to 12-membered, preferably 7- to 10-membered, bicyclic heterocyclic ring containing 1 to 3 oxygen atoms as ring constituent atoms; specifically, benzofuran, dihydrobenzofuran, chromane, benzodiozol, benzodioxane, etc.;

(e) a saturated or unsaturated 3- to 8-membered (preferably S— or 6-membered) monocyclic heterocyclic ring containing one sulfur atom as a ring constituent atom; specifically, thiophene, etc.;

(f) a saturated or unsaturated 7- to 12-membered, preferably 7- to 10-membered, bicyclic heterocyclic ring containing 1 to 3 sulfur atoms as ring constituent atoms; specifically, benzothiophene, etc.;

(g) a saturated or unsaturated 3- to 8-membered (preferably 5- or 6-membered) monocyclic heterocyclic ring containing 1 or 2 oxygen atoms and 1 to 3 nitrogen atoms as ring constituent atoms; specifically, oxazole, isoxazole, oxadiazole, morpholine, etc.;

(h) a saturated or unsaturated 7- to 12-membered, preferably 7- to 10-membered, bicyclic heterocyclic ring containing 1 or 2 oxygen atoms and 1 to 3 nitrogen atoms as ring constituent atoms; specifically, benzoxazole, dihydrobenzoxazole, benzoxadiazole, benzoisoxazole, benzoxazine, dihydrobenzoxazine, faropyridine, furopyrrole, benzoxazepine, tetrahydrobenzoxazepine, etc.;

(i) a saturated or unsaturated 3- to 8-membered (preferably 5- or 6-membered) monocyclic heterocyclic ring containing 1 or 2 sulfur atoms and 1 to 3 nitrogen atoms as ring constituent atoms; specifically, thiazole, thiazoline (dihydrothiazole), thiadiazole, isothiazole, thiazolidine, etc.;

(j) a saturated or unsaturated 7- to 12-membered, preferably 7- to 10-membered, bicyclic heterocyclic ring containing 1 or 2 sulfur atoms and 1 to 3 nitrogen atoms as ring constituent atoms; specifically, benzothiazole, dihydrobenzothiazole, benzothiadiazole, thienopyridine, imidazothiazole, dihydroimidazothiazole, thienopyrazine, benzothiazine, dihydrobenzothiazine, benzothiazepine, tetrahydrobenzothiazepine, etc.; and (k) a saturated or unsaturated 7- to 12-membered, preferably 7- to 10-membered, bicyclic heterocyclic ring containing 1 or 2 oxygen atoms and 1 to 3 sulfur atoms as ring constituent atoms; specifically, benzoxathiine, etc.;

and the like.

Examples of "heteroaryl" include a monocyclic or polycyclic aromatic ring containing 1 to 5 heteroatoms independently selected from the group consisting of nitrogen, oxygen and sulfur as ring constituent atoms, for example, a 3- to 15-membered monocyclic, bicyclic or tricyclic aromatic ring. Preferred heteroaryl is a 5- to 10-membered heteroaryl. Specific examples of heteroaryl include pyridyl, imidazolyl, triazolyl, indolyl, quinolinyl, oxazolyl, thiazolyl, etc.

Examples of "halogen" include fluorine, chlorine, bromine or iodine, preferably fluorine, chlorine or bromine. More preferred is fluorine or chlorine.

Each group defined herein may be linked to another group via a linker such as —O—, —C(═O)—, —C(═O)—O—, —S—, —S(═O)—, —S(═O)(═O)—, —O—C(═O)—, etc. as appropriate.

Examples of "substituent" in the term "an optionally substituted a" (wherein a refers to any group described herein) include at least one group independently selected from the group consisting of:

(A) a halogen,
(B) —CN,
(C) —$NO_2$,
(D) ═N—OH,
(E) —OH,
(F) —CHO,
(G) —COOH,
(H) —$SO_3H$.
(I) —$SO_2H$,
(J) —SH,
(K) ═O,
(L) ═S,
(M) an alkyl which may have at least one group independently selected from the substituent groups (Ia) and (Ib),
(N) an alkenyl which may have at least one group independently selected from the substituent groups (Ia) and (Ib),
(O) an alkynyl which may have at least one group independently selected from the substituent groups (Ia) and (Ib),
(P) an alkoxy which may have at least one group independently selected from the substituent groups (Ia) and (Ib),
(Q) an alkenyl-O— which may have at least one group independently selected from the substituent groups (Ia) and (Ib),
(R) an alkynyl-O— which may have at least one group independently selected from the substituent groups (Ia) and (Ib),
(S) an alkyl-CO— which may have at least one group independently selected from the substituent groups (Ia) and (Ib),
(T) an alkenyl-CO— which may have at least one group independently selected from the substituent groups (Ia) and (Ib),
(U) an alkynyl-CO— which may have at least one group independently selected from the substituent groups (a) and (Ib),
(V) an alkyl-COO— which may have at least one group independently selected from the substituent groups (Ia) and (Ib), (W) an alkoxy-CO— which may have at least one group independently selected from the substituent groups (Ia) and (Ib), (X) an alkyl-S— which may have at least one group independently selected from the substituent groups (Ia) and (Ib), (Y) an alkyl-SO— which may have at least one group independently selected from the substituent groups (Ia) and (Ib), (Z) an alkyl-$SO_2$— which may have at least one group independently selected from the substituent groups (Ia) and (Ib), (AA) a cycloalkyl which may have at least one group independently selected from the substituent groups (Ia), (Ib), (Ic) and =O, (BB) a cycloalkoxy which may have at least one group independently selected from the substituent groups (Ia), (Ib), (Ic) and =O, (CC) a cycloalkenyl which may have at least one group independently selected from the substituent groups (Ia), (Ib), (Ic) and =O, (DD) a cycloalkenyl-O— which may have at least one group independently selected from the substituent groups (Ia), (Ib), (Ic) and =O, (DE) a cycloalkyl-CO— which may have at least one group independently selected from the substituent groups (la), (Ib), (Ie) and =O, (FF) a cycloalkoxy-CO— which may have at least one group independently selected from the substituent groups (Ia); (Ib), (Ic) and =O, (GG) an aryl which may have at least one group independently selected from the substituent groups (Ia), (Ib) and (Ic), (HH) an aryl-O— which may have at least one group independently selected from the substituent groups (Ia), (Ib) and (Ic), (II) an aryl-CO— which may have at least one group independently selected from the substituent groups (Ia), (Ib) and (Ic), (JJ) an aryl-O—CO— which may have at least one group independently selected from the substituent groups (Ia), (Ib) and (Ic), (KK) an aralkyl which may have at least one group independently selected from the substituent groups (Ia), (Ib) and (Ic), (LL) an aralkyl-O— which may have at least one group independently selected from the substituent groups (Ia), (Ib) and (Ic), (MM) an aralkyl-CO— which may have at least one group independently selected from the substituent groups (Ia), (Ib) and (Ic), (NN) an aralkyl-O—CO— which may have at least one group independently selected from the substituent groups (Ia), (Ib) and (Ic), (OO) a heterocyclic ring group which may have at least one group independently selected from the substituent groups (Ia), (Ib), (Ic) and =O, (PP) a heterocyclic ring-O— which may have at least one group independently selected from the substituent groups (Ia), (Ib), (To) and =O, (QQ) a heterocyclic ring-CO— which may have at least one group independently selected from the substituent groups (Ia), (Ib), (Ic) and =O, (RR) a heterocyclic ring-O—CO— which may have at least one group independently selected from the substituent groups (Ia), (Ib), (Ic) and =O, (SS) an amino which may have at least one group independently selected from the substituent groups (Ia) and (Ic), and (TT) a carbamoyl which may have at least one group independently selected from the substituent groups (Ia) and (Ic).

The number of substituents in the compound of Formula (I) is not limited as long as it is chemically acceptable, but includes, for example, 1 to 10, 1 to 8, 1 to 6, 1 to 4, and 1 to 3. When o is an amino or carbamoyl, the number of substituents in a is 1 or 2. Substituents may also be attached to any atom, including carbon atoms and heteroatoms, as long as it is chemically acceptable.

The "substituent group (Ia)" is a group consisting of:

(a) an alkyl-CO— which may have at least one group independently selected from the substituent groups (IIa) and (IIb), (b) an alkenyl-CO— which may have at least one group independently selected from the substituent groups (IIa) and (IIb), (c) an alkynyl-CO— which may have at least one group independently selected from the substituent groups (IIa). and (IIb), (d) an alkoxy-CO— which may have at least one group independently selected from the substituent groups (IIa) and (IIb), (e) an alkyl-S— which may have at least one group independently selected from the substituent groups (IIa) and (IIb), (f) an alkyl-SO— which may have at least one group independently selected from the substituent groups (IIa) and (IIb), (g) an alkyl-$SO_2$— which may have at least one group independently selected from the substituent groups (IIa) and (IIb), (h) a cycloalkyl which may have at least one group independently selected from the substituent groups (IIa), (IIb), (IIc) and =O, (i) a cycloalkoxy which may have at least one group independently selected from the substituent groups (IIa), (IIb), (IIc) and =O, (j) a cycloalkenyl which may have at least one group independently selected from the substituent groups (IIa), (IIb), (IIc) and =O, (k) a cycloalkyl-CO— which may have at least one group independently selected from the substituent groups (IIa), (IIb), (IIc) and =O, (l) a cycloalkoxy-CO— which may have at least one group independently selected from the substituent groups (IIa), (IIb), (IIc) and =O, (m) an aryl which may have at least one group independently selected from the substituent groups (IIa), (IIb) and (IIc), (n) an aryl-CO— which may have at least one group independently selected from the substituent groups (IIa), (IIb) and (IIc), (o) an aryl-O—CO— which may have at least one group independently selected from the substituent groups (IIa), (IIb) and (IIc), (p) an aralkyl which may have at least one group independently selected from the substituent groups (IIa), (IIb) and (IIc), (q) an aralkyl-CO— which may have at least one group independently selected from the substituent groups (IIa), (IIb) and (IIc), (r) an aralkyl-O—CO— which may have at least one group independently selected from the substituent groups (IIa), (IIb) and (IIc),
(s) a heterocyclic ring group which may have at least one group independently selected from the substituent groups (IIa), (IIb), (IIc) and ═O,
(t) a heterocyclic ring-CO— which may have at least one group independently selected from the substituent groups (IIa), (IIb), (IIc) and ═O,
(v) a heterocyclic ring-O—CO— which may have at least one group independently selected from the substituent groups (IIa), (IIb), (IIc) and ═O, and
(w) a carbamoyl which may have at least one group independently selected from the substituent groups (IIa) and (IIc).

The "substituent group (Ib)" is a group consisting of:
(a) a halogen,
(b) —CN,
(c) —$NO_2$,
(d) —OH,
(e) —CHO,
(f) —COOH,
(g) —$SO_3H$,
(h) —SH,
(i) an alkoxy which may have at least one group independently selected from the substituent groups (IIa) and (IIb),
(j) an alkenyl-O— which may have at least one group independently selected from the substituent groups (IIa) and (IIb),
(k) an alkynyl-O— which may have at least one group independently selected from the substituent groups (IIa) and (IIb),
(l) an alkyl-COO— which may have at least one group independently selected from the substituent groups (IIa) and (IIb),
(m) a cycloalkenyl-O— which may have at least one group independently selected from the substituent groups (IIa), (IIb), (IIc) and ═O,
(n) an aryl-O— which may have at least one group independently selected from the substituent groups (IIa), (IIb) and (IIe),
(o) an aralkyl-O— which may have at least one group independently selected from the substituent groups (IIa), (IIb) and (IIc),
(p) a heterocyclic ring-O— which may have at least one group independently selected from the substituent groups (IIa), (IIb), (IIc) and ═O, and
(q) an amino which may have at least one group independently selected from the substituent groups (IIa) and (IIc).

The "substituent group (Ic)" is a group consisting
(a) an alkyl which may have at least one group independently selected from the substituent groups (IIa) and (IIb),
(b) an alkenyl which may have at least one group independently selected from the substituent groups (IIa) and (IIb), and
(c) an alkynyl which may have at least one group independently selected from the substituent groups (IIa) and (IIb).

The "substituent group (IIa)" is a group consisting of —CHO, alkyl-CO—, alkenyl-CO—, alkynyl-CO—, alkoxy-CO—, alkyl-$SO_2$—, cycloalkyl, cycloalkoxy, cycloalkenyl, cycloalkyl-CO—, cycloalkoxy-CO—, aryl, aryl-CO—, aryl-O—CO—, aralkyl, aralkyl-CO—, aralkyl-O—CO—, heterocyclic ring, heterocyclic ring-CO—, heterocyclic ring-O—CO—, mono- or di-(alkyl-CO)-carbamoyl, and mono- or di-alkylcarbamoyl.

The "substituent group (IIb)" is a group consisting of halogen, —CN, —$NO_2$, —OH, —COOH, —$SO_3H$, —SH, —$NH_2$, alkoxy, alkenyl-O—, alkynyl-O—, alkyl-COO—, alkyl-S—, alkyl-SO—, cycloalkenyl-O—, aryl-O—, aralkyl-O—, heterocyclic ring-O—, mono- or di-alkylamino, mono- or di-(alkyl-CO)-amino, mono- or di-alkoxycarbonylamino, mono- or di-arylcarbonylamino, and mono- or di-aralkylcarbonylamino.

The "substituent group (IIc)" is a group consisting of alkyl, alkenyl, and alkynyl.

The present invention includes the following embodiments:

Item 1. A compound represented by Formula [I]:

[Chemical formula 2]

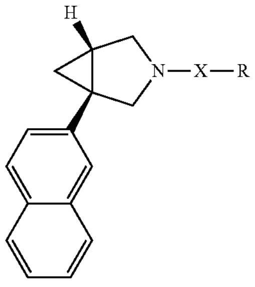

wherein
X is
1) —C(═O) —O—,
2) —C(═O)—O—C($X^{11a}$)($X^{12a}$)—O—C(═O)—,
3) —C(═O)—O—C($X^{11b}$)($X^{12b}$)—O—P(═O)(—O$R^{2b}$)—O—,
4) —C(═O)—,
5) —C(═O)—C($X^{11c}$($X^{12c}$)—N($X^{13c}$)—C(═O)—,
6) —C($X^{11d}$)($X^{12d}$)—O—C(═O)—,
7) —C($X^{11e}$)($X^{12e}$)—N($X^{13e}$)—C(═O)—,
8) —C($X^{11f}$)($X^{12f}$)—O—P(═O)(—O$R^{2f}$)—O—,
9) —C($X^{11g}$($X^{12g}$)—O—P(═O)(—O$R^{2g}$)—O—C($X^{11h}$)($X^{12h}$)—O—C(═O)—, or
10) —P(═O)(—O$R^{2i}$)—O—;

$X^{11a}$, $X^{11b}$, $X^{11c}$, $X^{11d}$, $X^{11e}$, $X^{11f}$, $X^{11g}$, $X^{11h}$, $X^{12a}$, $X^{12h}$, $X^{12c}$, $X^{12d}$, $X^{12e}$, $X^{12f}$, $X^{12g}$, and $X^{12h}$ are independently H or an optionally substituted $C_1$-$C_6$ alkyl, or
$X^{11a}$ and $X^{12a}$, $X^{11b}$ and $X^{12b}$, $X^{11c}$ and $X^{12c}$, $X^{11d}$ and $X^{12a}$, $X^{11e}$ and $X^{12e}$, $X^{11f}$ and $X^{12f}$, $X^{11g}$ and $X^{12g}$, and, $X^{11h}$ and $X^{12h}$ each may be taken together with a carbon atom to which they are both bonded to form a $C_3$-$C_6$ cycloalkane ring of a 3- to 6-membered heterocycloalkane ring;
$X^{13c}$ and $X^{13e}$ are independently H or an optionally substituted $C_1$-$C_6$ alkyl;
R, $R^{2b}$, $R^{2f}$, $R^{2g}$ and $R^{2f}$ are independently
i) H,
ii) an optionally substituted $C_1$-$C_{18}$ alkyl,
iii) an optionally substituted $C_2$-$C_{18}$ alkenyl,
iv) an optionally substituted $C_2$-$C_{18}$ alkynyl,
v) an optionally substituted 3- to 15-membered hydrocarbon ring group, or
vi) an optionally substituted 3- to 15-membered heterocyclic ring group,
or a salt thereof.

Item 2. The compound or salt thereof according to Item 1, wherein when R, $R^{2b}$, $R^{2f}$, $R^{2g}$ and $R^{2i}$ are substituted, each is optionally substituted by one or more, same or different groups independently selected from the group consisting of the followings:

1) a $C_1$-$C_6$ alkyl,
2) a hydroxy $C_1$-$C_6$ alkyl,
3) an optionally substituted $C_3$-$C_6$ cycloalkyl,
4) —C(═O)—O—$R^{11a}$,
5) —O—C(═O)—$R^{11b}$,
6) —C(═O)—N($R^{12a}$)—$R^{13a}$,
7) —N($R^{12b}$)—C(═O)—$R^{13b}$,
8) —N($R^{12c}$)—C(═O)—O—$R^{20}$,
9) —$SR^{14}$,
10) —$OR^{15}$,
11) —N($R^{12d}$)—$R^{16}$,
12) —S(═O)(═O)—$OR^{17}$,
13) —O—P(═O)($OR^{18}$)—$OR^{19}$,
14) an optionally substituted 6- to 14-membered aryl,
15) an optionally substituted 3- to 15-membered heterocyclic ring group,
16) a halogen, and
17) cyano, provided that, preferably, when R, $R^{2b}$, $R^{2f}$, $R^{2g}$ or $R^{2i}$ is ii) an optionally substituted $C_1$-$C_{18}$ alkyl,
iii) an optionally substituted $C_2$-$C_{18}$ alkenyl, or
iv) an optionally substituted $C_2$-$C_{18}$ alkynyl, the substituent of R, $R^{2b}$, $R^{2f}$, $R^{2g}$ and $R^{2i}$ is not 1) a $C_1$-$C_6$ alkyl, or
2) a hydroxy $C_1$-$C_6$ alkyl;

$R^{11a}$, $R^{11b}$, $R^{12a}$, $R^{12b}$, $R^{12c}$, $R^{12d}$, $R^{13a}$, $R^{13b}$, $R^{14}$, $R^{15}$, $R^{16}$, $R^{17}$, $R^{18}$, $R^{19}$and $R^{20}$ are independently H, an optionally substituted $C_1$-$C_6$ alkyl, an optionally substituted 3- to 15-membered hydrocarbon ring group, or an optionally substituted 3- to 15-membered heterocyclic ring group.

Item 3. The compound or salt thereof according to Item 1 or 2, wherein R, $R^{2b}$, $R^{2f}$, $R^{2g}$ and $R^{2i}$ are independently i) H,
ii) an optionally substituted $C_1$-$C_{18}$ alkyl,
iii) an optionally substituted $C_2$-$C_6$ alkenyl,
iv) an optionally substituted $C_2$-$C_6$ alkynyl,
v) an optionally substituted $C_3$-$C_6$ cycloalkyl,
vi) an optionally substituted 6- to 10-membered aryl, or
vii) an optionally substituted 5- to 10-membered heterocyclic ring group;

wherein when R, $R^{2b}$, $R^{2f}$, $R^{2g}$ and $R^{2i}$ are substituted, each is optionally substituted by 1 to 3, same or different groups independently selected from the group consisting of the followings:

1) a $C_1$-$C_6$ alkyl,
2) a hydroxy $C_1$-$C_6$ alkyl,
3) a $C_3$-$C_6$ cycloalkyl optionally substituted by 1 to 3, same or different $C_1$-$C_6$ alkyl,
4) —C(═O)—O—$R^{11a}$,
5) —O—C(═O)—$R^{11b}$,
6) —C(═O)—N($R^{12a}$)—$R^{13a}$,
7) —($R^{12b}$)—C(═O)—$R^{13b}$,
8) —N($R^{12c}$)—C(═O)—O—$R^{20}$,
9) —$SR^{14}$,
10) —$OR^{15}$,
11) —N($R^{12d}$)—$R^{16}$,
12) —S(═O)(═O)—$OR^{17}$,
13) —O—P(═O)($OR^{18}$)—$OR^{19}$,
14) an optionally substituted 6- to 10-membered aryl, wherein the optionally substituted 6- to 10-membered aryl is a 6- to 10-membered aryl optionally substituted by 1 to 3, same or different groups selected from the group consisting of a $C_1$-$C_6$ alkyl, a hydroxy $C_1$-$C_6$ alkyl and a $C_1$-$C_6$ alkanoyloxy,
15) an optionally substituted 5- to 10-membered heterocyclic ring group, wherein the optionally substituted 5- to 10-membered heterocyclic ring group is a 5- to 10-membered heterocyclic ring group optionally substituted by 1 to 3, same or different groups selected from the group consisting of a $C_1$-$C_6$ alkyl and a $C_1$-$C_6$ alkanoyloxy,
16) a halogen, and
17) cyano, provided that, preferably, when R, $R^{2b}$, $R^{2f}$, $R^{2g}$ and $R^{2i}$ is ii) an optionally substituted $C_1$-$C_{18}$ alkyl,
iii) an optionally substituted $C_2$-$C_6$ alkenyl, or
iv) an optionally substituted $C_2$-$C_6$ alkynyl, the substituent of R, $R^{2b}$, $R^{2f}$, $R^{2g}$ and $R^{2i}$ is not 1) a $C_1C_6$ alkyl, or
2) a hydroxy $C_1$-$C_6$ alkyl;

$R^{11a}$, $R^{11b}$, $R^{12a}$, $R^{12b}$, $R^{12c}$, $R^{12d}$, $R^{13a}$, $R^{13b}$, $R^{14}$, $R^{15}$, $R^{16}$, $R^{17}$, $R^{18}$, $R^{19}$and $R^{20}$ are independently H, an optionally substituted $C_1$-$C_6$ alkyl, an optionally substituted 6- to 10-membered aryl, or an optionally substituted 5- to 10-membered heteroaryl, wherein the optionally substituted $C_1$-C(alkyl is optionally substituted by 1 or 2, same or different groups selected from the group consisting of an optionally substituted phenyl and amino, the optionally substituted 6- to 10-membered aryl is optionally substituted by 1 to 3, same or different groups selected from the group consisting of a hydroxy $C_1$-$C_6$ alkyl and a $C_1$-$C_6$alkoxy, the optionally substituted 5- to 10-membered heteroaryl is optionally substituted by 1 to 3, same or different hydroxy $C_1$-$C_6$ alkyl, Item 4. The compound or salt thereof according to any one of Items 1-3, wherein X is —C(═O)—O—,
—C(═O)—O—C($X^{11a}$)($X^{12a}$)—O—C(═O)—,
—C(═O)—,
—C(═O)—C($X^{11c}$($X^{12c}$)—N($X^{13c}$)—C(═O)—, or
—P(═O)(—$OR^{2i}$)—O—;

$X^{11a}$, $X^{11c}$, $X^{12a}$ and $X^{12c}$ are independently H or $C_1$-$C_6$ alkyl;

$X^{13c}$ is $C_1$-$C_6$ alkyl;

R and $R^{2i}$ are independently an optionally substituted $C_1$-$C_{18}$ alkyl, or an optionally substituted $C_3$-$C_6$ cycloalkyl, wherein when R and $R^{2i}$ are substituted, they are optionally substituted by 1 or 2, same or different groups selected from the group consisting of —C(═O)—O—$R^{11a}$, —NH—C(═O)—O—$R^{20}$, —NH—$R^{16}$, and an optionally substituted 6- to 10-membered aryl, wherein the optionally substituted 6- to 10-membered aryl is optionally substituted by 1 to 3, same or different groups selected from the group consisting of a $C_1$-$C_6$ alkyl and a $C_1$-$C_6$ alkanoyloxy;

$R^{11a}$ is H, or an optionally substituted $C_1$-$C_6$ alkyl, wherein the optionally substituted $C_1$-$C_6$ alkyl is optionally substituted by a phenyl optionally substituted by 1 to 3, same or different $C_1$-$C_6$alkoxy;

$R^{16}$ is H, or a $C_1$-$C_6$ alkyl;

$R^{20}$ is a $C_1$-$C_6$ alkyl.

Item 5. The compound or salt thereof according to Item 4, wherein X is —C(═O)—O—, —C(═O)—O—C($X^{11a}$)($X^{12a}$)—O—C(═O)—, or —C(═O)—;

$X^{11a}$ and $X^{12a}$ are independently H or methyl.

Item 6. The compound or salt thereof according to any one of Items 1-5, for use in treating a central nervous system (CNS) disorder.

Item 7. A pharmaceutical composition comprising the compound or salt thereof according to any one of Items 1-5, and a pharmaceutically acceptable carrier.

Item 8. The pharmaceutical composition according to Item 7, for treating a central nervous system (CNS) disorder.

Item 9. Use of the compound or salt thereof according to any one of Items 1-5 or the composition according to Item 7 for the manufacture of a medicament for treating a central nervous system (CNS) disorder.

Item 10. A method for treating a central nervous system (CNS) disorder, comprising administering to a subject a therapeutically effective amount of the compound or salt thereof according to any one of Items 1 to 5, or the composition according to Item 7.

Item 11, A medicament for treating and/or preventing a central nervous system (CNS) disorder, comprising the compound or salt thereof according to any one of Items 1 to 5.

In a preferred embodiment of the present invention, R, $R^{2b}$, $R^{2f}$, $R^{2g}$ and $R^{2i}$ are independently i) H, ii) an optionally substituted $C_1$-$C_{18}$ alkyl, iii) an optionally substituted $C_2$-$C_6$ alkenyl, iv) an optionally substituted $C_2$-$C_6$ alkynyl, v) an optionally substituted $C_3$-$C_6$ cycloalkyl.

vi) an optionally substituted 6- to 10-membered aryl, or vii) an optionally substituted 5- to 10-membered heterocyclic ring group.

In a preferred embodiment of the present invention. disclosed is a compound represented by Formula [I]:

[Chemical formula 3]

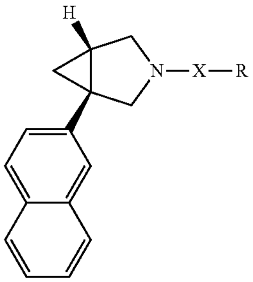

wherein

X is

1) —C(=O)—O—,

2) —C(=O)—O—C($X^{11a}$)($X^{12a}$)—O—C(=O)—,

3) —C(=O)—O—C($X^{11b}$)($X^{12b}$)—O—P(=O)(—O$R^{2b}$)—O—,

4) —C(=O)—,

5) —C(=O)—C($X^{11c}$)($X^{12c}$)—N($X^{13c}$)—C(=O)—,

6) —C($X^{11d}$)($X^{12d}$)—O—C(=O)—,

7) —C($X^{11e}$)($X^{12e}$)—N($X^{13e}$)—C(=O)—,

8) —C($X^{11f}$)($X^{12f}$)—O—P(=O)(—O$R^{2f}$)—O—,

9) —C($X^{11g}$)($X^{12g}$)—O—P(=O)(—O$R^{2g}$)—O—C($X^{11h}$)($X^{12h}$)—O—C(=O)—, or

10) —P(=O)(—O$R^{2i}$)—O—;

$X^{11a}$, $X^{11b}$, $X^{11c}$, $X^{11d}$, $X^{11e}$, $X^{11f}$, $X^{11g}$, $X^{11h}$, $X^{12a}$, $X^{12b}$, $X^{12c}$, $X^{12d}$, $X^{12e}$, $X^{12f}$, $X^{12g}$, and $X^{12h}$ are independently H or an optionally substituted $C_1$-$C_6$ alkyl, or $X^{11a}$ and $X^{12a}$, $X^{11b}$ and $X^{12b}$, $X^{11c}$ and $X^{12c}$, $X^{11d}$ and $X^{12d}$, $X^{11e}$ and $X^{12e}$, $X^{11f}$ and $X^{12f}$, $X^{11g}$ and $X^{12g}$, and, $X^{11h}$ and $X^{12h}$ each may be taken together with a carbon atom to which they are both bonded to form a $C_3$-$C_6$ cycloalkane ring or a 3- to 6-membered heterocycloalkane ring;

$X^{13c}$ and $X^{13e}$ are independently H or an optionally substituted $C_1$-$C_6$ alkyl;

R, $R^{2b}$, $R^{2f}$, $R^{2g}$ and $R^{2i}$ are independently i) H, ii) an optionally substituted $C_1$-$C_{18}$ alkyl, iii) an optionally substituted $C_2$-$C_6$ alkenyl, iv) an optionally substituted $C_2$-$C_6$ alkynyl, v) an optionally substituted $C_3$-$C_6$ cycloalkyl, vi) an optionally substituted 6- to 10-membered aryl, or vii) an optionally substituted 5- to 10-membered heterocyclic ring group;

wherein R, $R^{2b}$, $R^{2f}$, $R^{2g}$ and $R^{2i}$ each is optionally substituted by one or more, preferably 1 to 3, more preferably 1 to 2, same or different groups independently selected from the group consisting of the followings:

1) a $C_1$-$C_6$ alkyl, 2) a hydroxy $C_1$-$C_6$ alkyl, 3) an optionally substituted $C_3$-$C_6$ cycloalkyl (preferably, a $C_3$-$C_4$ cycloalkyl optionally substituted by 1 to 3 (preferably 1), same or different $C_1$-$C_6$ alkyl), 4) —C(=O)—O—$R^{11a}$, 5) —O—C(=O)—$R^{11b}$, 6) —C(=O)—N($R^{12a}$)—$R^{13a}$, 7) —N ($R^{12b}$)—C(=O)—$R^{13b}$, 8) —N($R^{12c}$)—C(=O)—O—$R^{20}$,

9) —S$R^{14}$,

10) —O$R^{15}$,

11) —N($R^{12d}$)—$R^{16}$,

12) —S(=O)(=O)—O$R^{17}$,

13) —O—P(=O)(O$R^{18}$)—O$R^{19}$, 14) an optionally substituted 6- to 10-membered aryl, wherein the optionally substituted 6- to 10-membered aryl is preferably a 6- to 10-membered aryl optionally substituted by 1 to 3, same or different groups selected from the group consisting of a $C_1$-$C_6$ alkyl, a hydroxy $C_1$-$C_6$ alkyl and a $C_1$-$C_6$ alkanoyloxy, wherein a preferable 6- to 10-membered aryl includes phenyl, 15) an optionally substituted 5- to 10-membered heterocyclic ring group, wherein the optionally substituted 5- to 10-membered heterocyclic ring group is preferably a 5- to 10-membered heterocyclic ring group optionally substituted by 1 to 3, same or different groups selected from the group consisting of a $C_1$-$C_6$ alkyl and a $C_1$-Ca alkanoyloxy, wherein a preferable 5- to 10-membered heterocyclic ring group includes 5- of 6-membered heterocyclic ring group, for example, selected from the group consisting of pyridyl and dihydropyridyl, 16) a halogen, and 17) cyano, provided that, preferably, when R, $R^{2b}$, $R^{2f}$, $R^{2g}$ or $R^{2i}$ is ii) an optionally substituted $C_1$-$C_{18}$ alkyl, iii) an optionally substituted $C_2$-$C_6$ alkenyl, or iv) an optionally substituted $C_2$-$C_6$ alkynyl, the substituent of R, $R^{2b}$, $R^{2f}$, $R^{2g}$ and $R^{2i}$ is not 1) a $C_1$-$C_6$ alkyl, or 2) a hydroxy $C_1$-$C_6$ alkyl;

$R^{11a}$, $R^{11b}$, $R^{12a}$, $R^{12b}$, $R^{12c}$, $R^{12d}$, $R^{13a}$, $R^{13b}$, $R^{14}$, $R^{15}$, $R^{16}$, $R^{17}$, $R^{18}$, $R^{19}$, and $R^{20}$ are independently H, an optionally substituted $C_1$-$C_6$ alkyl, an optionally substituted 6- to 10-membered aryl, or an optionally substituted 5- to 10-membered heteroaryl, wherein the optionally substituted $C_1$-$C_6$ alkyl is a $C_1$-$C_6$ alkyl, or a $C_1$-$C_6$ alkyl optionally substituted by 1 or 2, same or different groups selected from the group consisting of an optionally substituted phenyl and amino, wherein the optionally substituted phenyl is optionally substituted by 1 to 3, preferably 1, same or different $C_1$-$C_6$alkoxy, the optionally substituted 6- to 10-membered aryl is preferably a phenyl optionally substituted by 1 to 3, preferably 1, same or different groups selected from the group consisting of a hydroxy $C_1$-$C_6$ alkyl and a $C_1$-$C_6$alkoxy, the optionally substituted 5- to 10-membered heteroaryl is preferably a pyridyl optionally substituted by 1 to 3, preferably 1, same or different hydroxy $C_1$-$C_6$ alkyl, or a salt thereof.

In one embodiment of the present invention, X is —C(═O)—O—, —C(═O)—O—C($X^{11}$)($X^{12}$)—O—C(═O)—, —C(═O)—, —C(═O)—C($X^{11}$)($X^{12}$)N($X^{13}$)—C(═O)—, or —P(═O)(—$OR^2$)—O—;

$X^{11}$ and $X^{12}$ ace independently H or $C_1$-$C_6$ alkyl;

$X^{13}$ is a $C_1$-$C_6$ alkyl.

In one embodiment of the present invention, $R^{11a}$, $R^{11b}$, $R^{12a}$, $R^{12}$, $R^{12c}$, $R^{12d}$, $R^{13a}$, $R^{13b}$, $R^{14}$, $R^{15}$, $R^{16}$, $R^{17}$, $R^{18}$, $R^{19}$, and $R^{20}$ are independently H, an optionally substituted $C_1$-$C_6$ alkyl, an optionally substituted 3- to 15-membered hydrocarbon ring group, or an optionally substituted 3- to 15-membered heterocyclic ring group.

Preferably, $R^{11a}$, $R^{11b}$, $R^{12a}$, $R^{12b}$, $R^{12c}$, $R^{12d}$, $R^{13a}$, $R^{13b}$, $R^{14}$, $R^{15}$, $R^{16}$, $R^{17}$, $R^{18}$, $R^{19}$, and $R^{20}$ are independently H, an optionally substituted $C_1$-$C_6$ alkyl, an optionally substituted 6- to 10-membered aryl, or an optionally substituted 5- to 10-membered heteroaryl. More preferably, the optionally substituted $C_1$-$C_6$ alkyl is a $C_1$-$C_6$ alkyl, or when it is substituted, it is optionally substituted by 1 or 2, same or different groups selected from the group consisting of an optionally substituted phenyl and amino; the optionally substituted 6- to 10-membered aryl is optionally substituted by 1 to 3, same or different hydroxy $C_1$-$C_6$ alkyl, or $C_1$-$C_6$ alkoxy; the optionally substituted 5- to 10-membered heteroaryl is optionally substituted by 1 to 3, same or different hydroxy $C_1$-$C_6$ alkyl.

In one more preferred embodiment, $R^{11a}$, $R^{11b}$, and $R^{13b}$ are independently H; a $C_1$-$C_6$ alkyl optionally substituted by amino, phenyl, or a $C_1$-$C_6$ alkoxyphenyl; a phenyl optionally substituted by a $C_1$-$C_6$ alkyl, a hydroxy $C_1$-$C_6$ alkyl, or a $C_1$-$C_6$ alkoxy; or a pyridinyl optionally substituted hydroxy $C_1$-$C_6$ alkyl.

In one embodiment of the present invention, $R^{12a}$, $R^{12b}$, $R^{12c}$, $R^{12d}$, $R^{13a}$, $R^{14}$, $R^{15}$, $R^{16}$, and $R^{17}$ are independently H, or an optionally substituted $C_1$-$C_6$ alkyl. Preferably, $R^{12a}$, $R^{12b}$, $R^{12c}$, $R^{12d}$, $R^{13a}$, $R^{14}$, $R^{15}$, $R^{16}$, and $R^{17}$ are independently H, or $C_1$-$C_6$ alkyl.

In one embodiment of the present invention, $R^{18}$ and $R^{19}$ are independently H or an optionally substituted $C_1$-$C_6$ alkyl. Preferably, $R^{18}$ and $R^{19}$ are independently H, or $C_1$-$C_6$ alkyl.

In one embodiment of the present invention, $R^{20}$ is H or an optionally substituted $C_1$-$C_6$ alkyl. Preferably, $R^{20}$ is H, a $C_1$-$C_6$ alkyl optionally substituted by a $C_1$-$C_6$ alkyl or phenyl. More preferably, $R^{20}$ is a $C_1$-$C_6$ alkyl, or a $C_1$-$C_6$ alkyl optionally substituted by phenyl.

In one embodiment of the present invention, when R, $R^{2b}$, $R^{2f}$, $R^{2g}$, or $R^{2i}$ is an optionally substituted 3- to 15-membered hydrocarbon ring group, or has an optionally substituted 3- to 15-membered hydrocarbon ring group, the 3- to 15-membered hydrocarbon ring group is preferably an optionally substituted 6- to 14-membered aryl (e.g., 6- to 10-membered aryl); or an optionally substituted 3- to 14-membered saturated hydrocarbon ring (e.g., 3- to 10-membered saturated hydrocarbon ring). More preferably, the 3- to 15-membered hydrocarbon ring group is a phenyl optionally substituted by 1 to 3, same or different groups selected from the group consisting of a $C_1$-$C_6$ alkyl, a hydroxy $C_1$-$C_6$ alkyl, a $C_1$-$C_6$alkoxy, and a $C_1$-$C_6$ alkanoyloxy; or a $C_1$-$C_6$ cycloalkyl optionally substituted by 1 to 3, same or different groups selected from the group consisting of a $C_1$-$C_6$ alkyl, a $C_1$-$C_6$alkoxy-(C═O)—, a $C_1$-$C_6$ alkoxy-(C═O)—NH—, and amino. More preferably, the 3- to 15-membered hydrocarbon ring group is phenyl, hydroxymethylphenyl, methoxyphenyl, acetoxyphenyl, dimethylacetoxyphenyl, cyclopropyl, methylcyclopropyl, methoxycarbonylcyclopropyl, a $C_1$-$C_6$ alkoxy-(C═O)—NH-cyclopropyl, or aminocyclopropyl.

In one embodiment of the present invention, when R, $R^{2b}$, $R^{2f}$, $R^{2g}$, or $R^{2i}$ is an optionally substituted 3- to 15-membered heterocyclic ring group, or has an optionally substituted 3- to 15-membered heterocyclic ring group, the 3- to 15-membered heterocyclic ring group is preferably an optionally substituted 5- to 10-membered heterocyclic ring group. More preferably, the 3- to 15-membered heterocyclic ring group is a pyridinyl or dihydropyridinyl optionally substituted by a $C_1$-$C_6$ alkyl, a hydroxy $C_1$-$C_6$ alkyl, or a $C_1$-$C_6$ alkanoyloxy. Preferably, the 3- to 15-membered heterocyclic ring group is pyridinyl, methylpyridinyl, methyldihydropyridinyl, hydroxy methylpyridinyl, or acetoxypyridinyl.

The compound of Formula [I] is chemically or enzymatically converted to (1R,5S)-1-(naphthalen-2-yl)-3-azabicyclo[3.1.0]hexane under physiological conditions after administration to the body. The compound of Formula [I] may, for example, increase the water solubility of (1R,5S)-1-(naphthalen-2-yl)-3-azabicyclo[3.1.0]hexane, improve the bioavailability of the drug, and increase the selectivity of the drug to the target site.

In some embodiments, diseases that can be created by the compound of Formula [I] include those listed below, which can be treated by inhibiting the reuptake of multiple biogenic amines that are associated as causes of the target central nervous system disorders:

(i) attention deficit hyperactivity disorder (ADHD, both pediatric and adult) and related behavioral disorders, and alcohol abuse, drug abuse, obsessive-compulsive disorder, learning disability, reading disability, gambling addiction, manic symptoms, phobias, panic attack, oppositional defiant disorder, conduct disorder, disruptive behavior disorder, academic problems in school, smoking, aberrant sexual behavior, schizoid behavior, somatization, depression (including, but not limited to major depressive disorder, recurrent; dysthymic disorder; depressive disorder not otherwise specified (NOS); major depressive disorder, single episode; depression associated with bipolar disorder, Alzheimer's disease, psychosis or Parkinson's disease; postpartum depression; and seasonal affective disorder, etc.), sleep disturbances, generalized anxiety disorder, forms and symptoms of stuttering and tics (e.g., Tourette's disorder);

(ii) ADHD, substance abuse, depression, anxiety disorder (including, but not limited to panic disorder, generalized anxiety disorder, obsessive-compulsive disorder, post-traumatic stress disorder and social anxiety disorder, etc.), autism, traumatic brain injury, cognitive impairment, schizophrenia (especially with regard to cognition), obesity, chronic pain disorder, personality disorder and mild cognitive impairment;

(iii) anxiety disorder, panic disorder, post-traumatic stress disorder, obsessive-compulsive disorder, schizophrenia and related disorders, obesity, tics, addiction, Parkinson's disease and chronic pain;

(iv) substance abuse disorders (including, but not limited to alcohol-related disorder, nicotine-related disorder, amphetamine-related disorder, marijuana-related disorder, cocaine-related disorder, hallucinogen use disorder, inhalant-related disorder and opioid-related disorder, etc.);

(v) cognitive impairment, bipolar disorder, anorexia 30 nervosa, bulimia nervosa, mood-cycling disorder, chronic fatigue syndrome, chronic or acute stress, fibromyalgia and other somatoform disorders (somatization disorder, conversion disorder, pain disorder, hypochondria, somatoform disorder, undifferentiated somatoform disorder, somatoform NOS, etc.), incontinence (i.e., tension incontinence, true pressure incontinence, and mixed incontinence), inhalation disorders, mania, migraine headaches, peripheral neuropathy;

(vi) addictive disorders (including, but not limited to eating disorders, impulse control disorders, alcohol-related disorders, nicotine-related disorders, amphetamine-related disorders, cannabis-related disorders, cocaine-related disorders, hallucinogen use disorders, inhalant-related disorders, opioid-related disorders, etc.)

(vii) fragile X-associated disorders;

(viii) autism spectrum disorders (ASD), for example, in patients with fragile X-associated disorders;

(ix) ADHD in patients with fragile X-associated disorders)

(x) comorbidities of ADHD and depression;

(xi) comorbidities of ADHD and substance abuse;

(xii) comorbidities of ADHD and anxiety disorder.

In other embodiments, diseases that can be treated by the compound of Formula [I] include those listed below:

attention deficit hyperactivity disorder (ADHD) and related behavioral disorders, and substance abuse (alcohol abuse, drug abuse), compulsive behavior, learning disability, reading disability, gambling addiction, manic symptoms, phobias, panic attack, defiant behavior, conduct disorder, academic problems in school, smoking, aberrant sexual behavior, schizoid behavior, Somatization, depression, sleep disturbances, generalized anxiety disorder, forms and symptoms of stuttering and tics;

depression, anxiety disorder, autism, traumatic brain injury, cognitive impairment and schizophrenia (especially cognitive impairment), obesity, chronic pain disorder, personality disorder and mild cognitive impairment;

panic disorder, post-traumatic stress disorder, obsessive-compulsive disorder, schizophrenia and related disorders, obesity, tics, Parkinson's disease;

fragile X-associated disorders;

fragile X-associated disorders in patients who have failed prior fragile X-associated disorder treatment;

attention deficit/hyperactivity disorder (ADHD), for example, comorbidities (e.g., depression) with one or both anxiety disorder and depression in patients with fragile X-associated disorders;

autism spectrum disorder (ASD).

In yet other embodiments, disorders for which treatment using the compound of Formula [I] is considered include those listed in the Quick Reference to Diagnostic Criteria by the DSM-IV (Diagnostic and Statistical Manual of Mental Disorders, fourth edition), American Psychiatric Association, Washington, D.C., 1994. These target disorders include, but are not Limited to, attention-deficit/hyperactivity disorder, inattention-predominant; attention-deficit/hyperactivity disorder, hyperactive-impulsivity-predominant; attention-deficit/hyperactivity disorder, mixed; attention-deficit/hyperactivity disorder not otherwise specified (NOS); conduct disorder; oppositional defiant disorder; and disruptive conduct disorder not otherwise specified (NOS).

Depression disorders herein include, but are not limited to, major depressive disorder, repetitive; dysthymic disorder; depressive disorder not otherwise specified (NOS); and major depressive disorder, single episode.

Addictive disorders herein include, but are not limited to, eating disorder, impulse control disorders, alcohol-related disorders, nicotine-related disorders, amphetamine-related disorders, cannabis-related disorders, cocaine-related disorders, hallucinogen use disorders, inhalant-related disorders, and opioid-related disorders.

The present invention also includes, in addition to the aspects illustrated above, any combination of preferred aspects or alternatives for the different elements or features herein, as long as there is no contradiction.

General Production Method

The compound of Formula [I] can be manufactured, for example, according to the general synthetic methods described below, but are not limited thereto.

The starting material compounds may be commercially available products, or may be products manufactured according to methods known per se or those analogous thereto.

The solvents, acids, bases, protecting groups, and leaving groups used in the production of the compound of Formula [I] are not particularly limited as long as they are normally used in the field of synthetic organic chemistry.

In the manufacture of the compound of Formula [I], the product can be used as a reaction solution or as a crude product thereof in the next reaction. However, the product can be isolated from the reaction mixture in accordance with a conventional method, or easily purified by general separation means. Examples of the general separation means include filtration, extraction, concentration, distilling off, crystallization, recrystallization, reprecipitation, distillation, chromatography, and optical resolution.

In the manufacture of the compound of Formula [I], in the case of performing alkylation reaction, hydrolysis reaction, amination reaction, esterification reaction, amidation reaction, etherification reaction, oxidation reaction, reduction reaction, and the like, these reactions are performed according to methods known per se.

These various reaction agents and methods commonly used are described, for example, Organic Functional Group Preparations, 2nd edition, Academic Press, Inc. (1989); Comprehensive Organic Transformations, VCH Publishers Inc. (1989) written by P. G. M. Wuts; Greene's Protective Groups in Organic Synthesis, 4th edition, (2006) written by T. W. Greene; John Wiley & Sons; New York, 1991, P. 309 and the like.

In the general production method of the compound of Formula [I], starting material compounds, intermediate compounds, and the compound of Formula [I] may be in the form of a salt, and a target compound obtained in each reaction may also form a salt. If each compound is a free compound, it can be converted to its target salt by a method known per se. If the compound is a salt, it can be converted to its free form or other desired salt by a method known per SE.

Common Scheme

The compound of Formula [I] can be synthesized by using the method classified as Step A or Step B below.

Step A: Coupling Reaction

[Chemical formula 4]

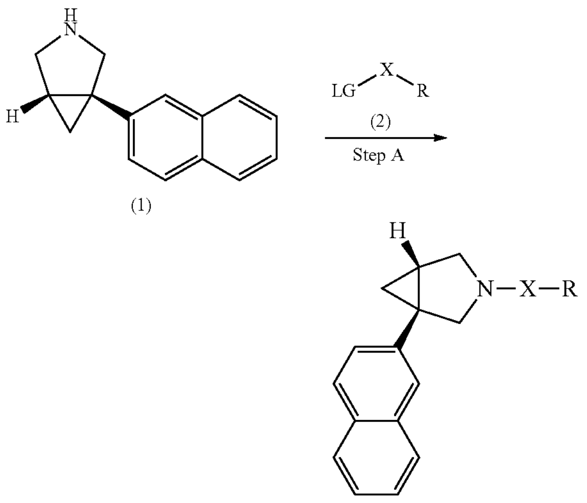

[I]

wherein LG represents a leaving group; other symbols are the same as above.

Step B: Dehydration-Condensation Reaction

[Chemical formula 5]

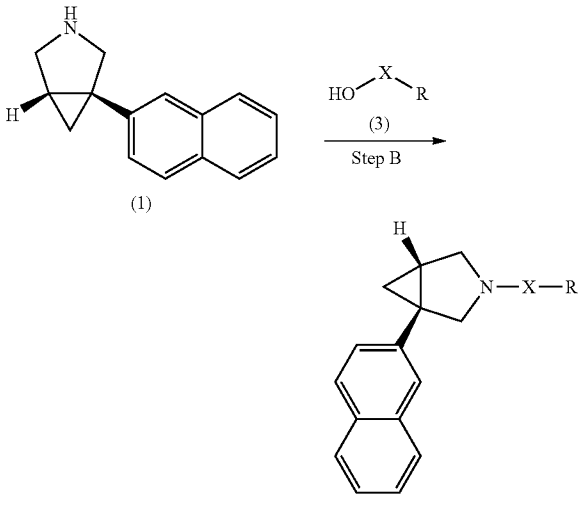

[I]

wherein each symbol is the same as above.

The compound of Formula [I] can be obtained by reacting Compound (1) with Compound (2) In an inert solvent, in the presence or absence of a base or acid depending on reaction conditions (Step A).

Alternatively, the compound of Formula [I] can be obtained by dehydration-condensation reaction of Compound (1) with Compound (3) in an inert solvent, in the presence or absence of a base and a condensing agent (Step B).

Compound (1) can be produced according to the method described in Patent Literature 1 and can be used in free or salt form. The salt forms of compound (1) include, for example, inorganic acids such as hydrochlorate, sulfate, carbonate, phosphate, hydrobromate, hydroiodate, nitrate; organic acids such as formate, propionate, oxalate, carbonate, picric acid, methanesulfonate, ethanesulfonate, p-toluenesulfonate, acetate, citrate, tartrate, malonate, succinate, maleate, fumarate, malate, lactate; and amino acids such as aspartate, glutamate.

Step A

The leaving group includes, for example, halogen atoms (e.g. chlorine, bromine, iodine), alkylsulfonyloxy groups (e.g. methylsulfonyloxy, ethylsulfonyloxy, trifluoromethylsulfonyloxy), arylsulfonyloxy groups (e.g. benzenesulfonyloxy, p-toluenesulfonyloxy, 2,4,6-trimethylbenzenesulfonyloxy, 2-nitrobenzenesulfonyloxy, 4-nitrobenzenesulfonyloxy, etc.), and the like.

The inert solvent includes, for example, water; alcohol solvents such as MeOH, EtOH, isopropanol, n-butanol, trifluoroethanol, ethylene glycol; ketone solvents such as acetone, methyl ethyl ketone; ether solvents such as THE, dioxane, $Et_2O$, diisopropyl ether, cyclopentyl methyl ether, diglyme; ester solvents such as AcOMe, AcOEt; nonprotic polar solvents such as MeCN, DME, DMSO; hydrocarbon solvents such as n-pentane, n-hexane, n-heptane, cyclohexane; halogenated hydrocarbon solvents such as methylene chloride, ethylene chloride, DCM; of other organic solvents; ox mixtures thereof.

As a base, for example, a wide range of known inorganic and organic bases can be used. Examples of the inorganic base include alkali metals (e.g., sodium, potassium, etc.), alkali metal hydrogen carbonates (e.g., lithium hydrogen carbonate, sodium hydrogen carbonate, potassium hydrogen carbonate, etc.), alkali metal hydroxides (e.g., LiOH, NaOH, KOH, etc.), alkali metal carbonates (e.g., $Li_2CO_3$, $Na_2CO_3$, $K_2CO_3$, $Cs_2CO_3$, etc.), alkali metal lower alkoxides (e.g. sodium methoxide, sodium ethoxide, etc.), and alkali metal hydrides (e.g. NaH, NaK, etc.). Examples of the organic base include trialkylamines (e.g., trimethylamine, triethylamine, N-ethyl diisopropylamine (DIPEA), etc.), pyridine, quinoline, piperidine, imidazole, picoline, dimethylaminopyridine, dimethylaniline, N-methylmorpholine, DBN, DABCO, DBU, etc.

If these bases are liquid, they can be used as a solvent. These bases may be used singly or in mixtures of two or more. The amount of base used is generally 0.1 to 10 moles, preferably 0.1 to 5 moles, per 1 mole of Compound (1).

The acid includes, for example, inorganic acids such as hydrochloric acid, sulfuric acid, nitric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluene sulfonic acid, 10-camphorsulfonic acid, etc. Two or more of these acids may be used in a mixture at an appropriate ratio. The amount of acid used is generally from 1 molar equivalent to an excess amount relative to Compound (1).

The reaction conditions are not limited, and the reaction can generally proceed under cooling, room temperature, or heating condition. Preferably, the reaction may be carried out at room temperature to 100° C. for 30 minutes to 30 hours, preferably 30 minutes to 5 hours.

Step B

The inert solvent includes, for example, the above inert solvents.

The base includes, for example, the above bases.

The condensing agent includes, for example, HATU; DCC; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N,N-diisopropylethylamine; WSC or its HCl salt; N,N'-carbonyl bis (2-methylimidazole); pentamethyleneketene-N-cyclohexylimine; diphenylketene-N-cyclohexylimine; ethoxyacetylene, 1-alkoxy-1-chloroethylene; trialkyl phosphite; ethyl polyphosphate; isopropyl polyphosphate; phosphorus oxychloride (phosphoryl chloride); phosphorus trichloride; diphenylphosphoryl azide; thionyl chloride; oxalyl chloride; alkyl haloformates, e.g. ethyl chloroformate, isopropyl chloroformate, etc; triphenylphosphine; 2-ethyl-7-hydroxy-benzisozazolium salt; 2-ethyl-5-(m-sulfophenyl)isoxazolium hydroxide, inner salt; benzotriazol-1-yloxy-tris(dimethylamino)phosphonium hexafluorophosphate; 1-(p-chlorobenzenesulfonyloxy)-6-chloro-1H-benzotriazole; Birsmeier's reagent prepared by the reaction of DMF with thionyl chloride, phosgene, trichloromethyl chloroformate, phosphorus oxychloride, etc.; and the like. The amount of condensing agent used is generally 1 to 10 molar equivalents, preferably 1 to 5 molar equivalents, relative to Compound (1).

In addition to the condensing agent, a condensation accelerator may be added. Examples of the condensation accelerator include 1-hydroxybenzotriazole (HOBt), N-hydroxysuccinimide (HOSu), 1-hydroxy-7-azabenzotriazole (HOAt), hydroxy-3,4-dihydro-4-oxo-1,2,3-benzotriazine (HOOBt), etc. The amount of condensation accelerator used is generally 0.1 to 10 molar equivalents, preferably 1 to 5 molar equivalents, relative to Compound (1).

The reaction conditions are not limited, and the reaction can generally proceed under cooling, room temperature, or heating condition. Preferably, the reaction may be carried out at room temperature to 100° C. for 30 minutes to 30 hours, preferably 30 minutes to 5 hours.

Synthesis of Carbamate Represented by Formula [I-1]

[Chemical formula 6]

[I-1]

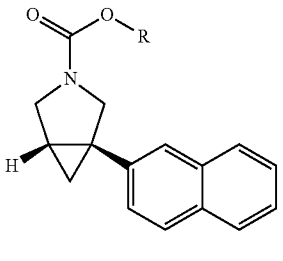

Among the compounds of Formula [I], the compound represented by Formula [I-1] can be synthesized more specifically by the process shown in Step A-1 below.

Step A-1: Coupling Reaction

[Chemical formula 7]

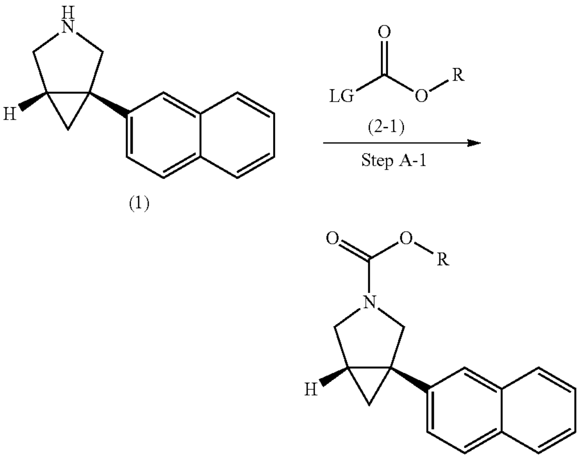

(1)

[I-1]

wherein each symbol is the same as above.

(Step A-1: (1)+(2-1)→[I-1])

The compound of Formula [I-1] can be obtained by reacting Compound (1) with Compound (2-1) in the presence of a base in an inert solvent.

The leaving group includes, for example, the above leaving groups.

The inert solvent includes, for example, the above inert solvents, preferably halogenated hydrocarbon solvents, e.g. dichloromethane.

The base includes, for example, the above bases, preferably tricthylamine.

The reaction conditions are not limited, and the reaction can generally proceed under cooling, room temperature, or heating condition, Preferably, the reaction may be carried out at room temperature to 100° C. for 30 minutes to 30 hours, preferably 30 minutes to 5 hours.

Synthesis of Acyloxymethylcarbamate Represented by Formula [I-2].

[Chemical formula 8]

[I-2]

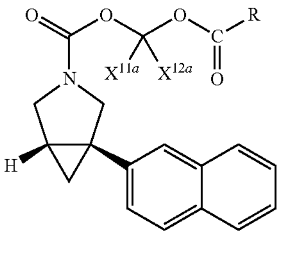

Among the compounds of Formula [I], the compound represented by Formula [I-2] can be synthesized more specifically by the processes shown in Steps C-2 and D-2 below.

Steps C-2 and D-2:Coupling Reaction

[Chemical formula 9]

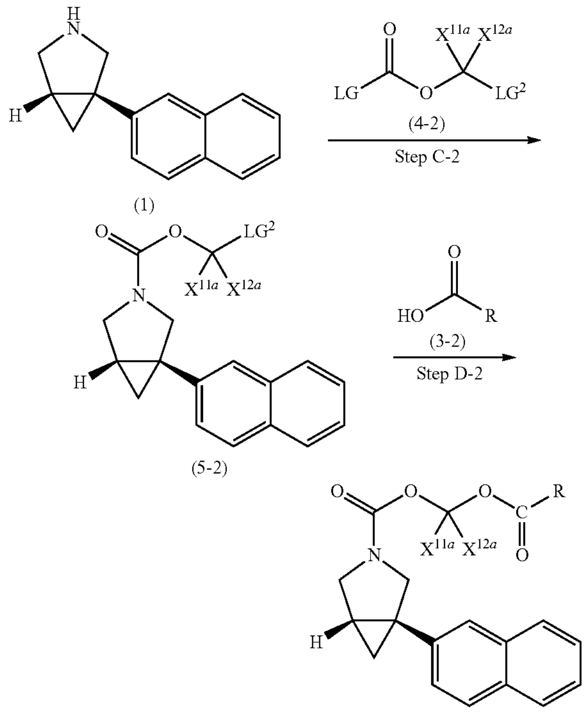

(1)

(5-2)

[I-2]

wherein LG and $LG^2$ each is a leaving group, and each symbol is the same as. above.

(Step C-2: (1)+(4-2)→(5-2))

(Step D-2: (5-2)+(3-2)→[I-2])

The compound of Formula [I-2] can be obtained by reacting Compound (1) with Compound (4-2) in the presence of a base in an inert solvent to give Compound (5-2), which is then reacted with Compound (3-2) in the presence of a base in an inert solvent.

Step C-2:Coupling Reaction (First Step)

The leaving group represented by LG includes, for example, the above leaving groups.

The inert solvent includes, for example, the above inert solvents, preferably halogenated hydrocarbon solvents, e.g. dichloromethane, The base includes, for example, the above bases, preferably triethylamine.

The reaction conditions are not limited, and the reaction can generally proceed under cooling, room temperature, or heating condition. Preferably, the reaction may be carried out at 0° C. to room temperature for 30 minutes to 30 hours, preferably 1 hour to 15 hours.

Step D-2:Coupling Reaction (Second Step)

The leaving group represented by LG2 includes, for example, the above leaving groups.

The inert solvent includes, for example, the above inert solvents, preferably N,N-dimethylformamide.

The base includes, for example, the above bases, preferably caesium carbonate.

The reaction conditions are not limited, and the reaction can generally proceed under cooling, room temperature, ox heating condition. Preferably, the reaction may be carried out at 0° C. to room temperature for 30 minutes to 30 hours, preferably 1 hour to 15 hours.

Synthesis of Amide Represented by Formula [I-4].

[Chemical formula 10]

[I-4]

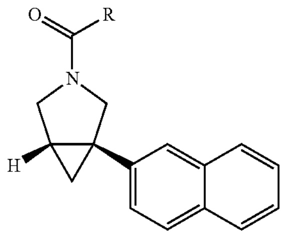

Among the compounds of Formula [I], the compound represented by Formula [I-4] can be synthesized more specifically by the processes shown in Steps A-4 and B-4 below.

Step A-4: Coupling Reaction

[Chemical formula 11]

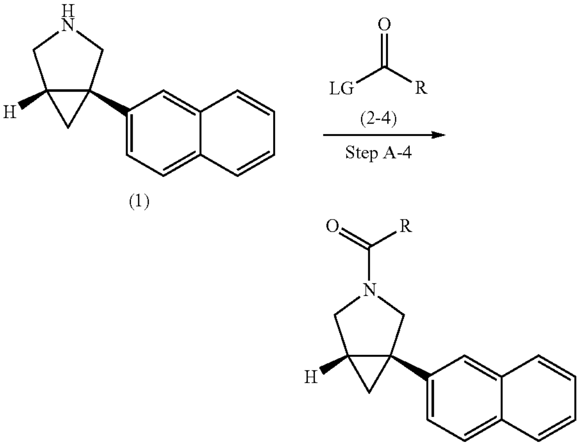

(1)

[I-4]

wherein each symbol is the same as above.

(Step A-4: (1)+(2-4)–[I-4])

The compound of Formula [I-4] can be obtained by reacting Compound (1) with Compound (2-4) in the presence of a base in am inert solvent.

The leaving group includes, for example, the above leaving groups.

The inert solvent includes, for example, the above inert solvents, preferably halogenated hydrocarbon solvents, e.g. dichloromethane.

The base Includes, for example, the above bases, preferably triethylamine.

The reaction conditions are not limited, and the reaction can generally proceed under cooling, room temperature, or heating condition, Preferably, the reaction may be carried out at room temperature to 100° C. for 30 minutes to 30 hours, preferably 30 minutes to 5 hours.

Step 8-4: Dehydration-Condensation Reaction

[Chemical formula 12]

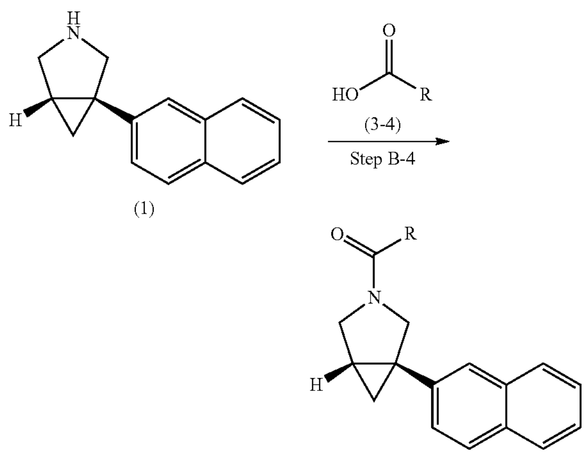

(1)

[I-4]

wherein each symbol is the same as above.

(Step B-4: (1)+(3-4)→[I-4])

The compound of Formula [I-4] can be obtained, for example, by amidation of Compound (1) and Compound (3-4). Specifically, Compound (I-4) can be synthesized by reacting Compound (1) of its salt with a reactive derivative at the carboxy group of Compound (3-4).

Suitable examples of the reactive derivative at the carboxy group of Compound (3-4) include acid halides, acid azides, acid anhydrides, activated amides, and activated esters. More preferred reactive derivatives include acid chlorides; acid azides, mixed acid anhydrides with acids such as substituted phosphoric acids (e.g. dialkyl phosphoric acid, phenyl phosphoric acid, diphenyl phosphoric acid, dibenzyl phosphoric acid, halogenated phosphoric acid, etc.), dialkyl phosphorous acid, sulfurous acid, thiosulfuric acid, sulfuric acid, sulfonic acids (e.g., methanesulfonic acid), aliphatic carboxylic acids (e.g., acetic acid, propionic acid, butyric acid, isobutyric acid, pivalic acid, pentanoic acid, isopentanoic acid, 2-ethylbutyric acid, trichloroacetic acid), or aromatic carboxylic acids (e.g., benzoic acid); symmetric acid anhydrides; activated amides with imidazole, 4-substituted imidazole, dimethylpyrazole, triazole or tetrazole; activated esters (e.g. cyanomethyl ester, methoxy methyl ester, dimethylimino methyl ester, vinyl ester, propargylic ester, p-nitrophenyl ester, 2,4-dinitrophenyl ester, trichlorophenyl ester, pentachlorophenyl ester, mesylphenyl ester, etc.); or esters with N-hydroxy compounds (e.g. N,N-dimethylhydroxylamine, 1-hydroxy-2-(1H)-pyridone, N-hydroxysuccinimide, N-hydroxyphthalimide, HOBt, etc.). These reactive derivatives can be selected arbitrarily among them according to the type of Compound (3-4) to be used.

When Compound (3B-4) is used in Step B-4 in the form of free acid or its salt, the reaction may be carried out in the presence of a condensing agent. HATU is preferred as the condensing agent in Step B-4. In the presence of the above condensing agent, the reaction may be carried out in the co-presence of an active esterifying agent such as N-hydroxysuccinimide, N-hydroxyphthalimide, HOBt, etc.

The inert solvent in Step B-4 includes, for example, the above inert solvents, preferably dimethylformamide.

The base in Step B-4 includes, for example, the above bases, preferably DIPEA.

The ratio of Compound (1) to Compound (3-4) in Step B-4 to be used is generally 1 mole of the former to at least 1 mole, preferably 1 to 5 moles, of the latter. The reaction temperature is not limited, and the reaction can generally proceed under cooling, room temperature, or heating condition. Preferably, the reaction may be carried out at room temperature to 100° C. for 30 minutes to 30 hours, preferably 30 minutes to 5 hours.

Synthesis of Phosphonate Represented by Formula [I-10].

[Chemical formula 13]

[I-10]

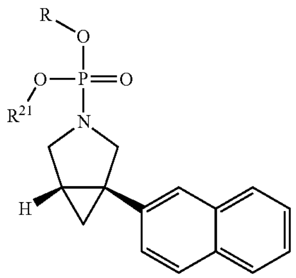

Among the compounds of Formula [I], the compound represented by Formula [I-10] can be synthesized more specifically by the processes shown in Step A-10 below.

Step A-10: Phosphate Coupling Reaction

[Chemical formula 14]

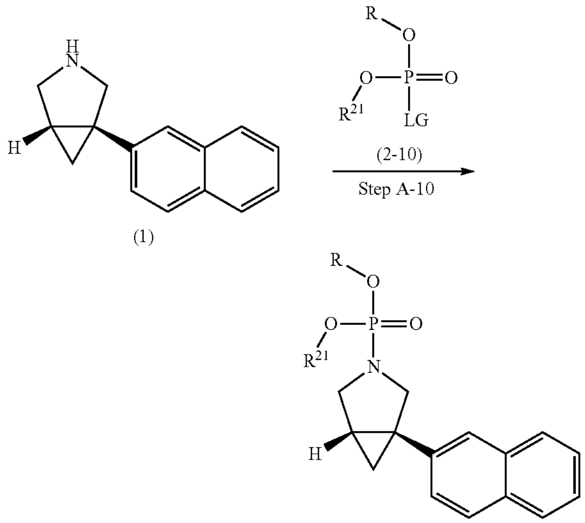

(1)

[I-10]

wherein each symbol is the same as above.

(Step A-10: (1)+(2-10)→[I-10])

The compound of Formula [I-10] can be obtained by reacting Compound (1) with Compound (2-10) in the presence of a base in an inert solvent.

The leaving group includes, for example, the above leaving groups.

The inert solvent includes, for example, the above inert solvents, preferably halogenated hydrocarbon solvents, e.g. dichloromethane.

The base includes, for example, the above bases, preferably DIPEA,

The reaction conditions are not limited, and the reaction can generally proceed under cooling, room temperature, or heating condition. Preferably, the reaction may be carried out at room temperature to 100° C. for 30 minutes to 30 hours, preferably 1 hour to 18 hours.

Production of Carboxylic Acid or Amine Compound

[Chemical formula 15]

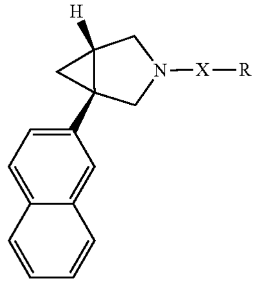

R: Ester
Hydrolysis
R: Carboxylic acid
R: Protected Amine
Deprotection
R: Amine wherein each symbol is the same as above.

The compound of Formula [I] wherein R contains a carboxylic acid may be synthesized as the final product by protecting the carboxylic acid group with an appropriate protecting group to form an ester or the like, and then performing either of the above steps to deprotect the protecting group. The compound of Formula [I] wherein R contains an amine may be synthesized as the final product by protecting the amine group with an appropriate protecting group, and then performing either of the above steps to deprotect the protecting group. There may be more than one, preferably one or two, carboxylic acids or amines in R.

Among the compounds of Formula [I], the compound represented by Formula [I-2'] can be synthesized, for example, by deprotection of the hydroxy-protecting group in Intermediate (6) using the process shown in Step E-2 below.

Step E-2: Deprotection of Hydroxy-Protecting Group (Hydrolysis Reaction)

[Chemical formula 16]

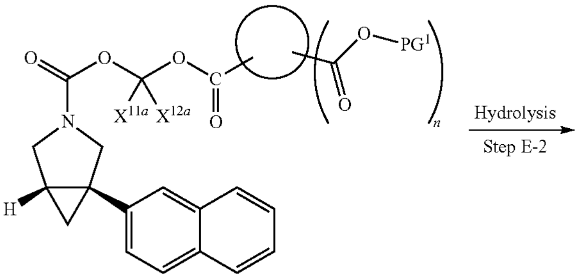

(6)

-continued

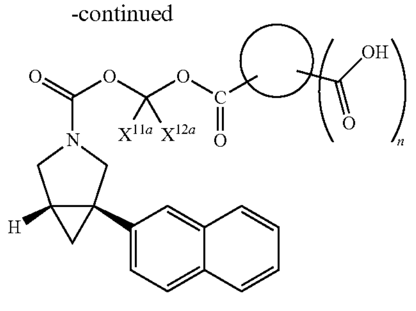

[1-2']

wherein $PG^1$ represents a protecting group of hydroxy group, the structure:

[Chemical formula 17]

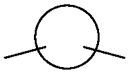

represents any group from the —X—R group excluding the structure shown in the above formula, n is any integer from 1 to 3, and each of the other symbols is the same as above.

(Step E-2: (6)→[I-2'])

Compound [I-2'] can be obtained by subjecting Intermediate (6) to a deprotection reaction, The deprotection reaction can be carried out by using any known reaction, and the known hydrolysis reaction may be applied. For example, if $PG^1$ is a silyl group, Intermediate (6) can be deprotected in the presence of a fluoride source or acid in an inert solvent to give Compound [I-2']. Alternatively, the deprotection reaction may be carried out by using a known hydrolysis reaction in the presence of a base.

Examples of the fluoride source include tetrabutylammonium fluoride, hydrofluoric acid, cesium fluoride, etc. The amount of fluoride source used is generally from 1 to 10 molar equivalents, preferably 1 to 5 molar equivalents, relative to Intermediate (6).

Examples of the acid include inorganic acids such as hydrochloric acid, sulfuric acid, nitric acid, hydrobromic acid, phosphoric acid, etc.; and organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc. These two or more acids may be mixed in appropriate proportions. The amount of acid used is generally from 1 molar equivalent to an excess amount relative to Intermediate (6).

Examples of the bass include inorganic bases such as alkali metal hydroxides (e.g., sodium hydroxide, potassium hydroxide), alkaline earth metal hydroxides (e.g., magnesium hydroxide, calcium hydroxide), alkali metal carbonates (e.g., sodium carbonate, potassium carbonate), alkaline earth metal carbonates (e.g., magnesium carbonate, calcium carbonate), alkali metal bicarbonates (e.g., sodium hydrogen carbonate, potassium hydrogen carbonate); and organic bases such as tri-alkylamine (e.g., trimethylamine, triethylamine), picoline, DBN, DABCO and DBU. Two or more of these may be used in a mixture at an appropriate ratio. The amount of acid used relative to intermediate (6) is generally from 1 molar equivalent to an excess amount.

Examples of the inert solvent include, for example, hydrocarbons, halogenated hydrocarbons, water, alcohols, ethers, esters, ketones, amides, nitriles, sulfoxides, etc. Two or more of these solvents may be used in a mixture at an appropriate ratio.

The reaction temperature is generally from −80 to 150° C. Reaction time is generally from 0.1 to 200 hours.

Examples of “protecting group of hydroxy group” or “hydroxy-protecting group” include, but are not limited to, those used in the field of synthetic organic chemistry, such as alkyl groups (e.g., methyl, ethyl, isopropyl, tert-butyl, trifluoromethyl, hydroxymethyl, 2-hydroxyethyl, acetylmethyl); alkenyl groups (e.g., ethenyl, 1-propenyl, 2-propenyl, 1-methyl-2-propenyl); alkynyl group (e.g., ethynyl, 1-propynyl, 2-propynyl, 1-methyl-2-propynyl); formyl group; alkyl(alkenyl)carbonyl groups (e.g., acetyl, propionyl, butyryl, isobutyryl, pentanoyl, pivaloyl, valeryl, isovaleryl, chloroacetyl, dichloroacetyl, trichloroacetyl, trifluoroacetyl, methoxyacetyl, acryloyl, propioloyl, methacryloyl, crotonoyl, isocrotonoyl, (E)-2-methyl-2-butenoyl); arylcarbonyl groups (e.g., benzoyl, α-naphthoyl, β-naphthoyl, 2-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, 4-phenylbenzoyl); alkoxycarbonyl groups (e.g., methoxycarbonyl, tert-butoxycarbonyl, 2,2,2-trichloroethoxycarbonyl, 2-trimethylsilylethoxycarbonyl, 9-flourenylmethyloxycarbonyl); tetrahydro(thio)pyranyl(foranyl) groups (e.g. , tetrahydropyran-2-yl, 3-bromotetrahydropyran-2-yl, 4-methoxytetrahydropyran-4-yl, tetrahydrothiopyran-2-yl, 4-methoxytetrahydrothiopyran-4-yl, tetrahydrofuran-2-yl, tetrahydrothiofuran-2-yl); silyl groups (e.g., trimethylsilyl, triethylsilyl, isopropyldimethylsilyl, tert-butyldimethylsilyl, methyl diisopropylsilyl, methyl di-tert-butylsilyl, triisopropylsilyl, diphenylmethylsilyl, diphenylbutylsilyl diphenylisopropylsilyl, phenyldiisopropylsilyl); alkoxymethyl groups (e.g., methoxymethyl, 1,1-dimethyl-1-methoxymethyl, ethoxymethyl, propoxymethyl, isopropoxymethyl, butoxymethyl, tert-butoxymethyl, 2-methoxyethoxymethyl, 2,2,2-trichloroethoxymethyl, bis (2-chloroethoxy)methyl); alkoxyethyl groups (e.g., 1-ethoxyethyl, 1-(isopropoxy)ethyl); ethyl halide groups (e.g., 2,2,2-trichloroethyl); aralkyl groups (e.g., benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4 methoxybenzyl, 4-methoxyphenyldiphenylmethyl, 2-nitrobenzyl, 4-nitrobenzyl, 4-chlorobenzyl, 4-bromobenzyl, 4-cyanobenzyl); alkenyloxycarbonyl groups (e.g., vinyloxycarbonyl, allyloxycarbonyl); aralkyloxycarbonyl groups (e.g., benzyloxycarbonyl, 4-methoxybenzyloxycarbonyl, 3,4-dimethoxybenzyloxycarbonyl, 2-nitrobenzyloxycarbonyl, 4-nitrobenzyloxycarbonyl); and the like. Preferred protecting group for hydroxy group includes alkyl groups.

Among the compounds of Formula [I], the compound shown in Formula [I-2"] can be synthesized by deprotecting the amine protecting group in Intermediate (7), for example, using the process shown in Step F-2 below.

Step F-2: Deprotection of Amine-Protecting Group

[Chemical formula 18]

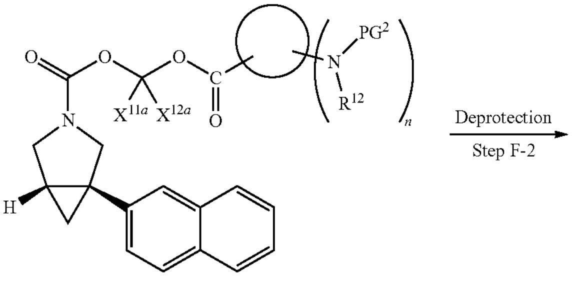

(7)

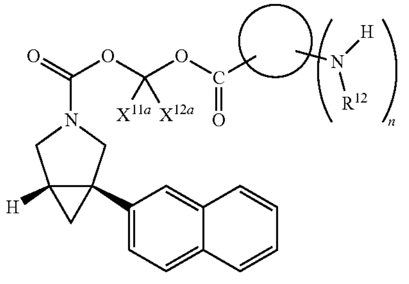

[1-2″]

wherein $PG^2$ represents a protecting group of amine, and each of the other symbols is the same as above, Compound [I-2"] can be obtained by subjecting Intermediate (7) to a deprotection reaction, For the deprotection reaction, any known reaction can be used. For example, when $PG^2$ is a tert-butoxycarbonyl group (Boc), Intermediate (7) can be deprotected in the presence of an acid (e.g., hydrochloric acid, trifluoroacetic acid, etc.) in an inert solvent or without a solvent to obtain Compound [I-2"].

The inert solvent includes, for example, hydrocarbons, halogenated hydrocarbons, water, alcohols, ethers (e.g. cyclopentyl methyl ether), esters, ketones, amides, nitriles, sulfoxides, etc. Two or more of these may be used in a mixture at an appropriate ratio.

The reaction temperature is generally from −80 to 150° C. The reaction time is generally from 0.1 to 200 hours.

Examples of “a protecting group of amine” or “amine-protecting group” include, but are not limited to, those used in the field of synthetic organic chemistry, such as “alkyl (alkenyl)carbonyl groups”, “arylcarbonyl groups”, “alkoxycarbonyl groups”, “silyl groups”, “aralkyl groups”, “alkenyloxycarbonyl groups” and “aralkyloxycarbonyl groups” in the above “protecting group of hydroxy group”. Preferred protecting group of amine includes Boc group.

Among the compound of Formula [I], the compound represented by Formula [I-4'] can be synthesized by deprotecting the amine-protecting group in Intermediate (8), for example, using the process shown in Step F-4 below:

Step F-4: Deprotection of Amine-Protecting Group

[Chemical formula 19]

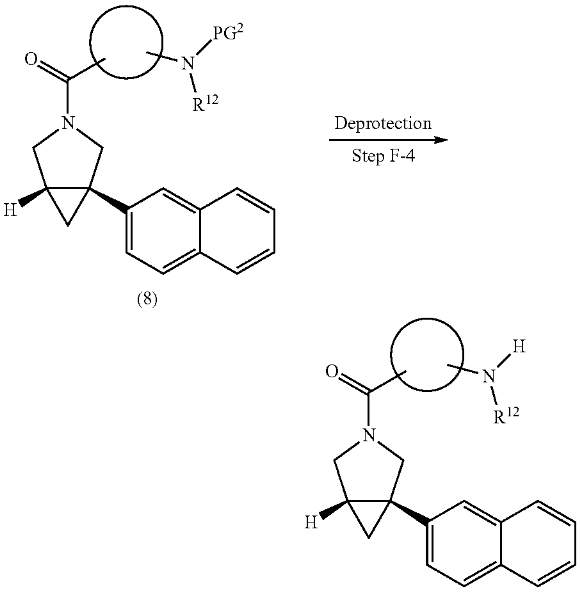

(8)

[1-4']

wherein each symbol is the same as above.

Compound [I-4'] can be obtained by subjecting Intermediate (8) to a deprotection reaction. The reaction can be carried out, for example, under the same reaction conditions as in Step F-2 above.

In the present description, the compound of Formula [I], starting material compounds and intermediate compounds include chemically acceptable geometric isomers, stereoisomers, optical isomers and tautomers. The isomers can be separated by general optical resolution methods or produced from the corresponding optically active starting material compound.

In the present description, the compound of Formula (I), starting material compounds and intermediate compounds may also be in the form of a salt, and a target compound obtained in each reaction may also form a salt. If a compound obtained in each reaction is a free compound, it can be converted to its target salt by a method known per se, and if the compound is a salt, it can be converted to its free form or other target salt by a method known per se, Such salts include those exemplified below.

In the present description, salts include pharmaceutically acceptable acid addition salts or base addition salts. The acid in the acid addition salts includes, for example, inorganic acids such as hydrochloric acid, hydrobromic acid, hydroiodic acid, nitric acid, sulfuric acid, phosphoric acid, etc.; organic acids such as formic acid, propionic acid, oxalic acid, carbonic acid, picric acid, methanesulfonic acid, ethanesulfonic acid, p-toluenesulfonic acid, acetic acid, citric acid, tartaric acid, malonic acid, succinic acid, maleic acid, fumaric acid, malic acid, lactic acid, etc.; amino acids such as aspartic acid, glutamic acid, etc.; and the like. The base in the base addition salts includes, for example, metals such as alkali metals (e.g. sodium, potassium, etc.), alkaline earth metals (e.g. calcium, magnesium, etc.), etc.; inorganic bases such as alkali metal carbonates (e.g., lithium carbonate, potassium carbonate, sodium carbonate, cesium carbonate, etc.), alkali metal hydrogen carbonates (e.g., lithium hydrogen carbonate, sodium hydrogen carbonate, potassium hydrogen carbonate, etc.), alkali metal hydroxides (e.g., lithium hydroxide, sodium hydroxide, potassium hydroxide, calcium hydroxide, cesium hydroxide, etc.); organic bases such as methylamine, diethylamine, trimethylamine, triethylamine, N-ethyl diisopropylamine, ethanolamine, diethanolamine, triethanolamine, ethylenediamine, tris(hydroxymethyl)methylamine, dicyclohexylamine, N,N'-dibenzylethylenediamine, quanidine, pyridine, quinoline, piperidine, imidazole, dimethylamino pyridine, dimethylaniline, picoline, choline, N-methylmorpholine, DBN, DBU, DASCO, etc.; amino acids such as lysine, arginine, etc.; ammonia; and the like.

The compound of Formula [I] also includes various hydrates, solvates, and crystalline polymorphs of the compounds represented by Formula [I] and salts thereof.

The compound of Formula [I] includes a compound in which any one or more atoms are substituted by one or more isotopes. Examples of the isotope include deuterium ($^2H$), tritium ($^3H$), $^{13}C$, $^{15}N$, $^{18}O$, and the like.

The compound of Formula [I] may be concomitantly used 25 with various therapeutic of prophylactic agents for the above diseases that can be treated by the compound of Formula [I]. The concomitant drugs may be administered simultaneously, or separately, consecutively or at desired time intervals, The simultaneous administration formulation may be in a combination formulation or formulated separately.

A pharmaceutical formulation comprising the compound of Formula [I] as an active ingredient (hereinafter referred to as "pharmaceutical composition") is described below.

The above pharmaceutical formulation is a formulation of the compound of Formula [I] in the form of a general pharmaceutical formulation, and is prepared by using the compound of Formula [I] or its salt and a pharmaceutically acceptable carrier. The carrier includes diluents or excipients which are generally used, for example, fillers, bulking agents, binders, humectants, disintegrants, surface active agents, lubricants, etc.

Such pharmaceutical formulation can be selected from various forms such as tablets, pills, dispersions, liquids, suspensions, emulsions, granules, capsules, suppositories, and injections (liquids, suspensions, etc.), depending on the therapeutic purpose.

In forming tablets, a wide range of known carriers can be used. Examples of the carrier include excipients such as lactose, white sugar, sodium chloride, glucose, urea, starch, calcium carbonate, kaolin, crystalline cellulose, etc.; binders such as water, ethanol, propanol, simple syrup, glucose solution, starch solution, gelatin solution, carboxymethyl cellulose, shellac, methyl cellulose, potassium phosphate, polyvinyl pyrrolidone, etc.; disintegrants such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, etc.; disintegration inhibitors such as white sugar, stearin, cocoa butter, hydrogenated oil, etc.; absorption enhancers such as quaternary ammonium base, sodium lauryl sulfate, etc.; moisturizers such as glycerin, starch, etc.; adsorbents such as starch, lactose, kaolin, bentonite, colloidal silicate, etc.; lubricants such as purified talc, stearate, boric acid powder, polyethylene glycol, etc.; and the like.

Furthermore, the tablets can be made into tablets with general tablet skins, e.g., sugar-coated tablets, gelatin-coated tablets, enteric-coated tablets, film-coated tablets or double-layered tablets, or multilayered tablets, if necessary.

In forming pills, a wide range of known carriers can be used. Examples of the carrier include excipients such as glucose, lactose, starch, cocoa butter, hardened vegetable oil, kaolin, talc, etc.; disintegrants such as gum arabic powder, tragacanth powder, gelatin, ethanol, etc.; laminaran, agar, etc.; and the like, In forming suppositories, a wide range of known carriers can be used. Examples of the carrier include polyethylene glycol, cocoa butter, higher alcohols, esters of higher alcohols, gelatin, semi-synthetic glycerides, etc.

Liquids, emulsions, and suspensions are preferably sterilized and isotonic to blood when prepared as injections. Diluents used in these liquids, emulsions, and suspensions can be any known and widely used diluents, such as water, ethanol, propylene glycol, ethoxylated isostearyl alcohol, polyoxylated isostearyl alcohol, polyoxyethylene sorbetan fatty acid esters, and the like. In this case, they may contain salt, glucose, amino acid, or glycerin in amounts sufficient to prepare an isotonic solution, and may also contain general solubilizing agents, buffers, soothing agents, etc., and further, if necessary, coloring agents, preservatives, flavorings, flavoring agents, sweetening agents, etc. and other medicines.

In the present description, the "therapeutically effective amount" refers to the amount effective to provide therapeutic benefit, such as symptom relief, when administered to humans or non-humans. The specific dose of a substance administered to provide therapeutic benefit will, of course, be determined by the specific environment, e.g., the specific substance to be administered, the route of administration, the condition to be treated and the individual to be treated. For example, the amount of the compound of Formula [I] contained in a pharmaceutical formulation may be 1 to 70% by weight of the compound of Formula [I] in the pharmaceutical formulation.

For example, for oral administration, the dosage that may give satisfactory results are of the order of about 0.01 to 20 mg/kg. The indicated daily dosage for oral administration ranges from about 0.75 mg to 2000 mg and may suitably be administered once a day or in two to four divided doses. Thus, a unit dosage form for oral administration may contain from about 0.2 mg to 100 mg or 500 mg, for example, from about 0.2 mg or 2.0 mg or 50 mg ox 75 mg or 100 mg to 200 mg or 500 mg of the compound of Formula [I], together with a pharmaceutically acceptable diluent or carrier.

In the present description, the "pharmaceutically acceptable" refers to a compound, or a composition comprising the compound, or a dosage form thereof, within a range with a reasonable benefit/risk ratio that does not cause excessive toxicity, irritation, allergic response, etc. and is suitable for application to humans or animals.

EXAMPLES

The present invention is explained in detail in the following by referring to Reference Examples, Examples, and Test Examples, which are not to be construed as limitative, and the invention may be changed within the scope of the present invention.

In the present description, the following abbreviations may be used.

REX: Reference example number

EX: Example number

STR: Structural formula

RProp: Manufacturing method (numbers indicate that the compound was manufactured using the corresponding raw materials in the same way as the reference example compound having that number as a reference example number)

Prop: Manufacturing method (numbers Indicate that the compound was manufactured using the corresponding raw materials in the same way as the example compound having that number as an example number)

Data: Physical property data (NMR1: δ (ppm) in $^1$H-NMR in dimethyl sulfoxide-$d_6$; NMR2: δ (ppm) in $^1$H-NMR in $CDCl_3$), NMR3: δ (ppm) in $^1$H-NMR in $CD_3OD$); or MS: Mass spectrum)

For compound names and reagents, the following abbreviations may be used.

TABLE 1

| Abbreviations | Words |
|---|---|
| 9-BBN | 9-borabicyclo[3.3.1]nonane |
| AcOEt | ethyl acetate |
| AcOH | acetic acid |
| AcOMe | methyl acetate |
| AcONa | sodium acetate |
| $BBr_3$ | boron tribromide |
| CDI | 1,1'-carbonyldiimidazole |
| CPME | cyclopentyl methyl ether |
| $Cs_2Co_3$ | cesium carbonate |
| DABCO | 1,4-diazabicyclo[2.2.2]octane |
| DBN | diazabicyclononene |
| DBU | 1,8-diazabicyclo[5.4.0]-7-undecene |
| DCC | dicyclohexylcarbodiimide |
| DCE | 1,2-dichloroethane |
| DCM | dichloromethane |
| DEAD | diethylazodicarboxylate |
| DHP | 3,4-dihydro-2H-pyran |
| DIBAL | diisobutylaluminum hydride |
| DIBOC | di-t-butyl decarbonate |
| DIPEA | diisopropylethylamine |
| DMA | N,N-DIMETHYLACETAMIDE |
| DMAP | 4-(dimethylamino)pyridine |
| DME | dimethoxyethane |
| DMF | N,N-dimethylformamide |
| DMSO | dimethyl sulfoxide |
| DPPA | diphenylphosphoryl azide |
| $Et_2O$ | diethyl ethyl |
| EtOH | ethanol |
| HATU | 1-[bis(dimethylamino)methylene]-1H-1,2,3-triazolo[4,5-b]pyridinium 3-oxid hexafluorophosphate |
| HCl | hydrochloric acid |
| Hexane | n-hexane |
| HOSu | N-hydroxysuccinimide (NHS) |
| HOAt | 1-hydroxy-7-azabenzotriazole |
| HOBt | 1-hydroxybenzotriazole |

TABLE 2

| | |
|---|---|
| HOOBt | hydroxy-3,4-dihydro-4-oxo-1,2,3-benzotriazine |
| IPA | 2-propanol |
| IPE | diisopropyl ether |
| $K_2CO_3$ | potassium carbonate |
| $K_3PO_4$ | tripotassium phosphate |
| $KHCO_3$ | potassium hydrogen carboate |
| KOH | potassium hydroxide |
| LAH | lithium aluminum hydride |
| LDA | lithium diisopropylamide |
| LHMDS | lithium hexamethyldisilazide |
| LiOH | lithium hydroxide |
| MCPBA | m-chloroperoxybenzoic acid |
| MeCN | acetonitrile |
| MEK | 2-butanone |
| MeOH | methanol |
| $NaBH_4$ | sodium borohydride |

TABLE 2-continued

| | |
|---|---|
| NaH | sodium hydride |
| $NaHCO_3$ | sodium hydrogen carbonate |
| NaOH | sodium hydroxide |
| NaOtBu | sodium t-butoxide |
| n-BuLi | n-butyllithium |
| NCS | N-chlorosuccinimide |
| NMP | N-methylpyrrolidone |
| Pd/C | palladium-carrying carbon |
| PEG | polyethylene glycol |
| PPTS | pyridinium p-toluenesulfonate |
| TEA | triethylamine |
| TFA | trifluoroacetic acid |
| THF | tetrahydrofuran |
| WSC | 3-ethyl-1-(3-dimethylaminopropyl) carbodiimide |
| WSC•HCl | 3-ethyl-1-(3-dimethylaminopropyl) carbodiimide hydrochloride |
| ZCl | benzyl chloroformate |

In the following Examples, "room temperature" generally means about 10° C. to about 35° C. The ratios indicated for mixed solvents are volume mixing ratios, unless otherwise specified. % means wt %, unless otherwise specified.

$^1$HNMR (proton nuclear magnetic resonance spectrum) was measured by Fourier-transform type NMR (either of Bruker AVANCE III 400 (400 MHz) and Bruker AVANCE III HD (500 MHz)).

Mass spectrum (MS) was measured by LC/MS (Acquity SQD/LC, Waters, Acquity UPLC H-Class, Waters, or ITQ 1100, Thermo Fisher scientific). The data indicates actual measured value (found). Generally, molecular ion peaks ($[M+H]^+$, $[M-H]^-$, etc.) of the free molecule, molecular ion peak $[M]^+$ or fragment ion peak of the free molecule, or sodium adduction peak $[M+Na]^+$ of the free molecule, etc. are observed.

The absolute configuration of the compound was determined by known X-Ray crystal structure analysis method (e.g., "Basic Course for Chemists 12, X-Ray Crystal Structure Analysis" written by Shigeru Ohba and Shigenobu Yano, 1st edition, 1999) or estimated from the empirical rule of Shi asymmetric epoxidation (Waldemar Adam, Rainer T. Fell, Chantu R. Saha-Moller and Cong-Gui Zhao: Tetrahedron: Asymmetry 1998, 9, 397-401; Yuanming Zhu, Yong Tu, Hongwu Yo, Yian Shi: Tetrahedron Lett. 1988, 29, 2437-2440).

Reference Example 1

(1R,5S)-1-(naphthalen-2-yl)-3-azabicyclo[3.1.0]hexane hydrochloride (2 g) and triethylamine (3.4 mL) were dissolved in DCM (40 mL). To the solution was slowly added chloromethyl ester (0.91 mL) with stirring under ice-cooling. The mixture was brought to room temperature and stirred for another 1 hour. To the reaction mixture was added water and the mixture was stirred. The organic layer was separated and concentrated under reduced pressure. The crude product was purified by silica gel column chromatography (Hexane-AcOEt) to give chloromethyl (1R,5S)-1-(naphthalen-2-yl)-3-azabicyclo[3.1.0]hexane-3-carboxylate (2.37 g).

Reference Example 3

Sebacic acid (10 g) was suspended in DCM (200 mL). DMF (0.38 mL) was added thereto, and the mixture was stirred. To this solution, oxalyl chloride (13 mL) was added slowly dropwise. After completion of the dropwise addition, the mixture was stirred at room temperature, The reaction mixture was concentrated under reduced pressure and azeotroped twice with DCM. The residue was dissolved in DCM (100 mL), and a solution of 4-methoxybenzyl alcohol (6.78 mL) in DCM (5 mL) was added dropwise thereto. After completion of the dropwise addition, the mixture was stirred at room temperature for 3 hours. The reaction mixture was stirred under ice-cooling, and 5 mol/L HCl was added dropwise thereto, and the mixture was stirred at room temperature overnight, The insoluble material was filtered off and the organic layer was separated from the filtrate. The organic layer was concentrated under reduced pressure and the residue was dissolved in AcOEt. The organic layer was washed twice with water, and then the organic layer was separated and concentrated under reduced pressure. The resulting solid was recrystallized with diethyl ether-hexane, and the crystals were filtered off. After drying under reduced pressure, 10-((4-methoxylbenzyl)oxy)-10-oxodecanoic acid (2.72 g) was obtained, Reference Example 4

4-Methoxybenzyl alcohol (5.99 mL) and oxepane-2,7-dione (80% purity, 5.0 g) were dissolved in DCM (200 mL), and DMAP (0.38 g, 3.1 mmol) and pyridine (6.82 mL) were added thereto. Then, the mixture was stirred at room temperature overnight.

To the reaction mixture was added 67 mL of 2 mol/L HCl aqueous solution. After stirring for a while, the organic layer was separated and then washed with saturated brine. The organic layer was separated and the solvent was removed under reduced pressure. The crude product obtained was purified by silica gel column chromatography (Hexane-ACOEt) to give 6-((4-methoxybenzyl)oxy)-6-oxo-oxo-hexanoic acid (3.21 g).

Reference Example 5

(1R,5S)-1-(naphthalen-2-yl)-3-azabicyclo[3.1.0]hexane hydrochloride (737 mg), N-(tert-butoxycarbonyl)-N-methyl glycine (624 mg), HATU (1.26 g), DIPEA (1.10 mL), DMF (7.5 mL), and DMF (7.5 mL) were mixed and stirred at room temperature for 18 hours. To the reaction mixture was added water, and the mixture was extracted with AcOEt. The extract was washed with 1 mol/L HCl aqueous solution, water, and saturated $NaHCO_3$ aqueous solution. The organic layer was dried over anhydrous magnesium sulfate, filtered, and the filtrate was concentrated under reduced pressure. The residue was purified by silica gel column chromatography (Hexane/AcOEt), and the solvent was concentrated under reduced pressure to give tert-butyl methyl(2-((1R,5S)-1-(naphthalen-2-yl)-3-azabicyclo[3.1.0]hexane-3-yl)-2-oxoethyl) carbamate (0.97 g).

Reference Example 6

Tert-butyl methyl(2-((1R,5S)-1-(naphthalen-2-yl)-3-azabicyclo[3.1.0]hexane-3-yl)-2-oxoethyl) carbamate (0.97 g) was dissolved in CPME, and 4 mol/L HCl CPME solution was added thereto at room temperature. Then, the mixture was stirred overnight. The solvent was concentrated under reduced pressure, The residue was triturated with EtOH and AcOEt, and the precipitated solid was filtered off. The solid was washed with AcOEt and dried to give 2-(methylamino)-1-((1R,5S)-1-(naphthalen-2-yl)-3-azabicyclo[3.1.0]hexane-3-yl)ethan-1-one hydrochloride.

Example 1

(1R,5S)-1-(naphthalen-2-yl)-3-azabicyclo[3.1.0]hexane hydrochloride (0.5 g) and TEA (0.85 mL) were dissolved in DCM (10 mL), and butyryl chloride (0.32 mL) was slowly added thereto with stirring under ice-cooling. The mixture was brought to room temperature and stirred for another 1 hour. To the reaction mixture was added water and the mixture was stirred. The organic layer was separated and concentrated under reduced pressure, The crude product was purified by silica gel column chromatography (Hexane-AcOEt) to give 1-((1R,5S)-1-(naphthalen-2-yl)-3-azabicyclo[3.1.0]hexane-3-yl) butan-1-one (550 mg).

Example 5

(1R,5S)-1-(naphthalen-2-yl)-3-azabicyclo[3.1.0]hexane hydrochloride (0.5 g) and TEA (0.85 mL) were dissolved in DCM (10 mL), and ethyl chloroformate (0.29 mL) was slowly added thereto with stirring under ice-cooling. The mixture was brought to room temperature and stirred for another 1 hour. To the reaction mixture was added water and the mixture was stirred. The organic layer was separated and concentrated under reduced pressure. The crude product was purified by silica gel column chromatography (Hexane-AcOEt). The resulting solid was recrystallized with diethyl ether-hexane and dried under reduced pressure to give ethyl (1R,5S)-1-(naphthalen-2-yl)-3-azabicyclo[3.1.0]hexane-3-carboxylate (320 mg).

Example 8

Chloromethyl(1R,5S)-1-(naphthalen-2-yl)-3-azabicyclo [3.1.0]hexane-3-carboxylate (the product of Reference Example 1) (0.50 g) was dissolved in 5 mL of DMF. To the mixture were added AcOH (0.19 mL) and $Cs_2CO_3$ (1.62 g), and the mixture was stirred at room temperature for 1 hour, To the reaction mixture were added water and ACOEt, and the mixture was stirred. The organic layer was separated and concentrated under reduced pressure. The crude product was purified by silica gel column chromatography (Hexane-AcOEt) to give acetoxymethyl (1R,5S)-1-(naphthalen-2-yl)-3-azabicyclo[3.1.0]hexane-3-carboxylate (510 mg).

Example 17

To 4-methoxybenzyl (((((1R,5S)-1-(naphthalen-2-yl)-3-azabicyclo[3.1.0]hexane-3-carbonyl)oxy)methyl)adipate (1.2 g) was added TFA (1.74 mL), and the mixture was stirred at room temperature for 1 hour, The reaction solution was concentrated under reduced pressure and then azeotroped twice with DCE. The crude product obtained was purified by silica gel column chromatography (Hexane-ACOEt) to give 6-(((((1R,5S)-1-(naphthalen-2-yl)-3-azabicyclo[3.1.0]hexane-3-carbonyl)oxy)methoxy)-6-oxo-hexanoic acid (463 mg).

Example 21

To 1-((tert-butoxycarbonyl)amino)cyclopropane-1-carbonyl)oxy)methyl (1R,5S)-1-(naphthalen-2-yl)-3-azabicyclo [3.1.0]hexane-3-carboxylate (0.70 g) was added TFA (1.16 mL), and the mixture was stirred at room temperature for 1 hour, To the reaction mixture was added DCM, and the mixture was concentrated under reduced pressure twice. The resulting residue was dissolved in a small amount of DCM and stirred, and 4 mol/L HCl AcOEt solution was added thereto and the mixture was stirred. To the mixture were added Hexane and diethyl ether, and the resulting solid was filtered off. After drying under reduced pressure, ((1-aminocyclopropane-1-carbonyl)oxy)methyl (1R,5S)-1-(naphthalen-2-yl)-3-azabicyclo[3.1.0]hexane-3-carboxylate hydrochloride (580 mg) was obtained.

Example 24

N2,N6-bis(tert-butoxycarbonyl)-L-lysine (1.45 g) and HOBt (0.94 g) were dissolved in DCM (20 mL). To the mixture were added (1R,5S)-1-(naphthalen-2-yl)-3-azabicyclo[3.1.0]hexane hydrochloride (1.0 g) and WSC·HCl (1.2 g), and the mixture was stirred at room temperature for 1 hour. To the reaction mixture was added water, and the mixture was stirred. Then, the organic layer was separated and concentrated under reduced pressure. The residue was purified by silica gel column chromatography (Hexane-AcOEt) to give di-tert-butyl ((S)-6-((1R,5S)-1-(naphthalen-2-yl)-3-azabicyclo[3.1.0]hexane-3-yl)-6-oxohexane-1,5-diyl)dicarbanate (1.81 g).

Example 27

(1R,5S)-1-(naphthalen-2-yl)-3-azabicyclo[3.1.0]hexane hydrochloride (123 mg), 3-(2-acetoxy-4,6-dimethylphenyl)-3-methyl butanoic acid (145 mg), HATU (209 mg), and DIPEA (0.183 mL) and DMF (1.5 mL) were mixed, and the mixture was stirred at room temperature for 18 hours. To the reaction mixture was added water, and the mixture was extracted with AcOEt. The extract was washed with 1N HCl aqueous solution, water, and saturated NaHCO, aqueous solution. The organic layer was dried over anhydrous magnesium sulfate, filtered, and the filtrate was concentrated under reduced pressure. The residue was purified by silica gel column chromatography (Hexane-ACOEt) to give 3,5-dimethyl-2-(2-methyl-4-((1R,5S)-1-(naphthalen-2-yl)-3-azabicyclo[3.1.0]hexane-3-yl)-4-oxobutan-2-yl)phenylacetate (189 mg).

Example 28

(1R,5S)-1-(naphthalen-2-yl)-3-azabicyclo[3.1.0]hexane hydrochloride (246 mg) and DIPEA (0.367 mL) were dissolved in DCM (2.5 mL). To the mixture was added diethylphosphorochloridate (0.159 mL), and the mixture was stirred at room temperature for 18 hours, To the reaction mixture was added water, and the mixture was extracted with DCM. The extract was washed with 1N HCl aqueous solution, water, and saturated $NaHCO_3$ aqueous solution. The organic layer was dried over anhydrous magnesium sulfate, filtered, and the filtrate was concentrated under reduced pressure. The residue was purified by silica gel column chromatography (Hexane-ACOEt) to give diethyl ((1R,5S)-1-(naphthalen-2-yl)-3-azabicyclo[3.1.0]hexane-3-yl)phosphonate (149 mg).

Example 29

A mixture of tert-butyl tert-butyl (2-(methyl(2-((1R,5S)-1-(naphthalen-2-yl)-3-azabicyclo[3.1.0]hexane-3-yl)-2-oxoethyl)amino)-2-oxoethyl)carbamate (0.47g) and 4N HCl CPME solution (2.4 mL) was stirred at room temperature for 15 hours. The solvent was concentrated under reduced pressure and triturated with IPE. The solid was filtered off and washed with hexane to give 2-(tert-butylamino)-N-methyl-N-(2-((1R,5S)-1-(naphthalen-2-yl)-3-azabicyclo[3.1.0]hexane-3-yl)-2-oxoethyl)acetamide hydrochloride (363 mg).

The structures and physical properties of the reference example compounds (Reference Examples 1-8) and the example compounds (Examples 1-30) obtained by processes similar to those described above, and the compounds (Examples 31-114) obtained by similar processes are shown in the following tables.

TABLE 3

| REX | STR |
|---|---|
| 1 | 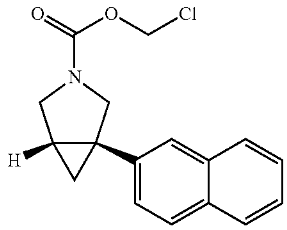 |
| 2 | 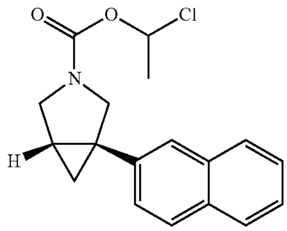 |
| 3 | 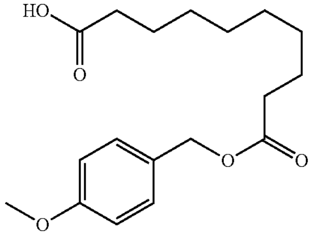 |
| 4 | 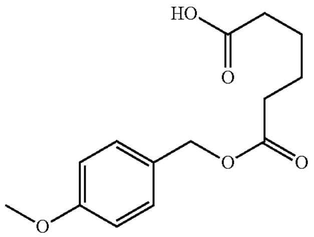 |
| 5 | 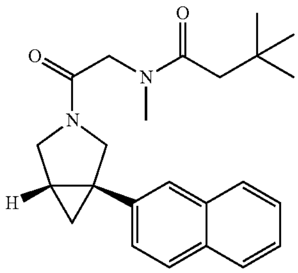 |

TABLE 3-continued

| REX | STR |
|---|---|
| 6 | 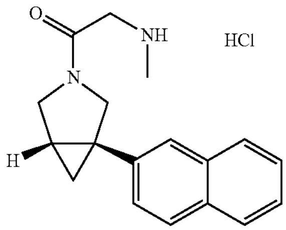 |
| 7 | 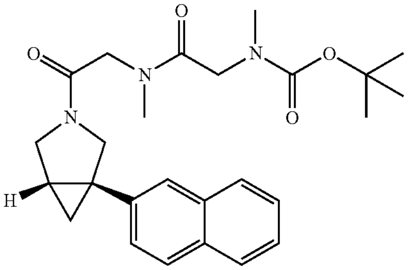 |
| 8 | 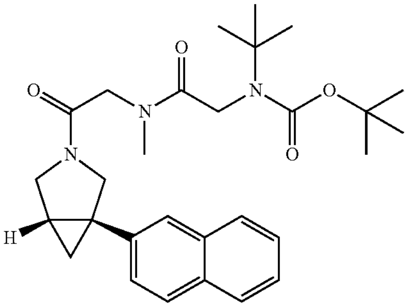 |

TABLE 4

| REX | RProp | Data |
|---|---|---|
| 1 | 1 | NMR2; 0.91 (d, J = 4.8 Hz, 1 H), 1.23-1.29 (m, 1 H), 1.97-2.02 (m, 1 H), 3.67-3.74 (m, 1 H), 3.78-3.90 (m, 2 H), 4.07-4.19 (m, 1 H), 7.26 (d, J = 8.6 Hz, 1 H), 7.42-7.51 (m, 2 H), 7.64 (s, 1 H) 7.76-7.83 (m, 3 H) |
| 2 | 1 | NMR2; 0.89-0.97 (m, 1 H), 1.23-1.27 (m, 1 H), 1.83 (s, 3 H), 1.97-2.01 (m, 1 H) 3.71-3.91 (m, 3 H), 4.00-4.21 (m, 1 H), 6.60-6.63 (m, 1 H), 7.24-7.28 (m, 2 H) 7.64 (s, 1 H), 7.77-7.81 (m, 3 H) |
| 3 | 3 | NMR2; 1.25-1.38 (m, 8 H), 1.57-1.65 (m, 4 H), 2.27-2.38 (m, 4 H), 3.81 (s, 3 H), 5.04 (s, 2 H), 6.88 (d, J = 8. 4 Hz, 2 H), 7.29 (d, J = 8.4 Hz, 2 H) |
| 4 | 4 | NMR2; 1.66-1.69 (m, 4 H), 2.34-2.38 (m, 4 H), 3.81 (s, 3 H), 5.05 (s, 2 H), 6.89 (d, J = 8.4 Hz, 2 H), 7.29 (d, J = 8.4 Hz, 2 H) |
| 5 | 5 | NMR2; 0.83-0.96(1H, br), 1.22-1.31(1H, m), 1.40-1.52(9H, m), 1.94-2.12(1H, m), 2.93-3.01(3H, m), 3.62-4.40(6H, m), 7.23-7.32(1H, m), 7.40-7.54(2H, m), 7.60-7.69(1H, m), 7.73-7.86(3H, m). |
| 6 | 6 | NMR2; 0.89(1H, br), 1.17(1H, br), 1.44(9H, s), 1.50(6H, s), 1.80-2.07(1H, m), 3.60-3.87(2H, m), 4.15-4.28(1H, m), 4.38-4.50 (1H, m), 4.98(1H, br), 7.22-7.33(1H, m), 7.40-7.52 (2H, m), 7.66(1H, s), 7.75-7.84(3H, m). |
| 7 | 5 | NMR2; 0.87-0.97(1H, m), 1.22-1.32(1H, m), 1.38-1.53(9H, m), 1.93-2.08(1H, m), 2.90-2.97(3H, m), 2.97-3.13(3H, m), 3.62-4.36(8H, m), 7.23-7.32(1H, m), 7.41-7.53(2H, m), 7.62-7.68 (1H, m), 7.74-7.86(3H, m). |
| 8 | 5 | NMR2; 0.84-1.00(1H, 3), 1.05(9H, s), 1.22-1.33(1H, m), 1.36-1.52(9H, m), 1.94-2.11(1H, m), 2.98- |

TABLE 4-continued
| REX | RProp | Data |
|---|---|---|
| | | 3.24(3H, m), 3.60-4.36(5H, m), 4.53-4.71(2H, m), 5.22-5.38(1H, m), 7.20-7.32(1H, m), 7.40-7.53(2H, m), 7.61-7.67(1H, m), 7.73-7.86(3H, m). |
TABLE 5
| EX | STR |
|---|---|
| 1 | 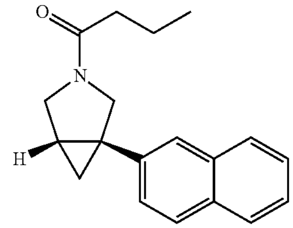 |
| 2 | 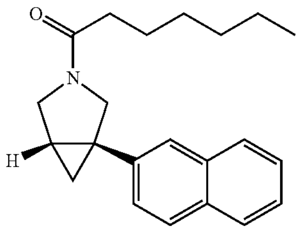 |
| 3 | 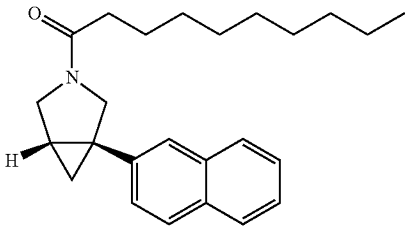 |
| 4 | 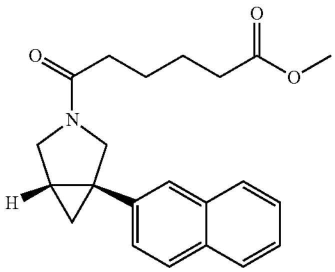 |
| 5 | 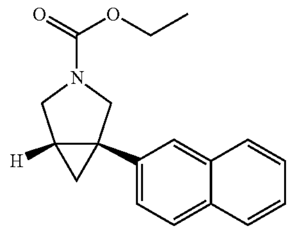 |
TABLE 5-continued
| EX | STR |
|---|---|
| 6 | 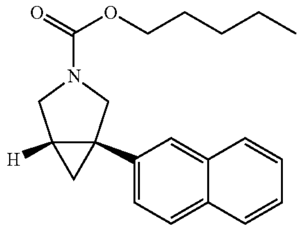 |
| 7 | 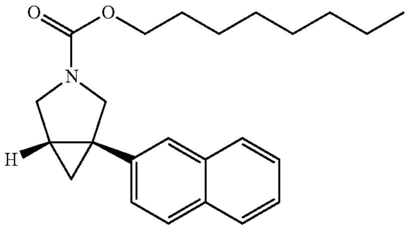 |
| 8 | 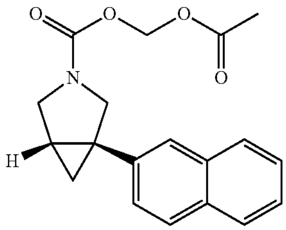 |
| 9 | 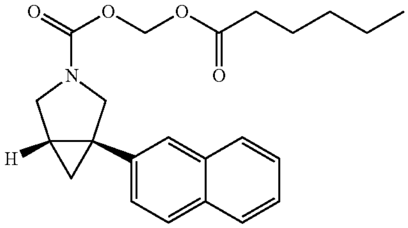 |
| 10 | 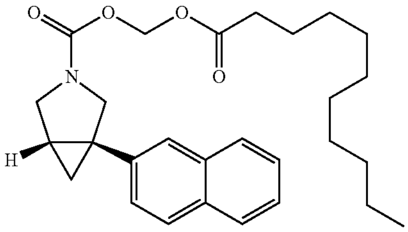 |

TABLE 5-continued
| EX | STR |
|---|---|
| 11 | 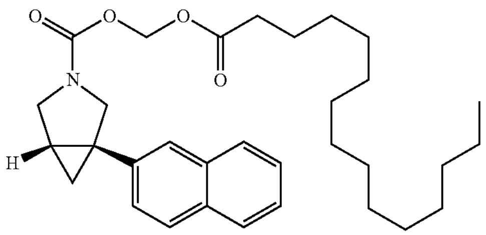 |
| 12 | 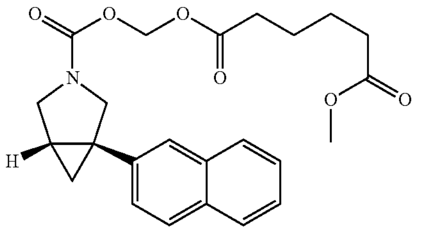 |
TABLE 5-continued
| EX | STR |
|---|---|
| 13 | 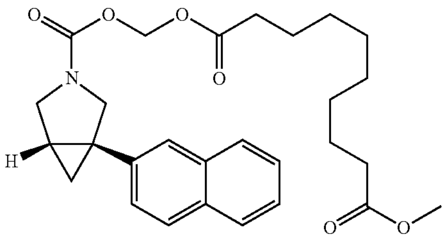 |
| 14 | 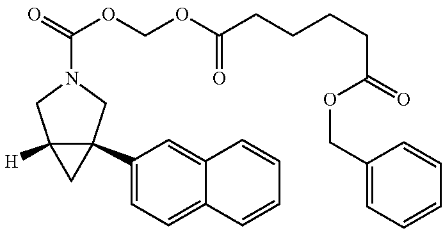 |
TABLE 6
| | |
|---|---|
| 15 | 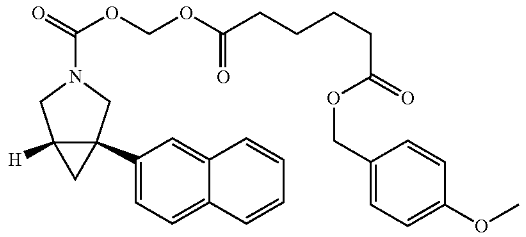 |
| 16 | 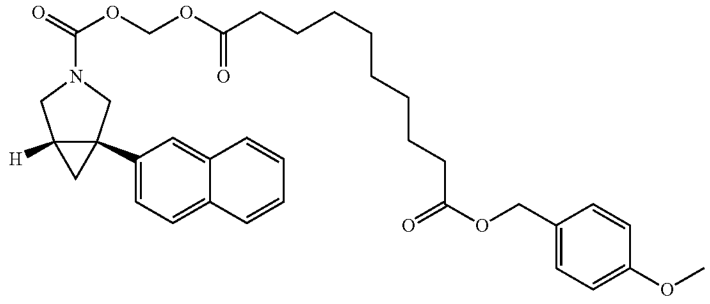 |
| 17 | 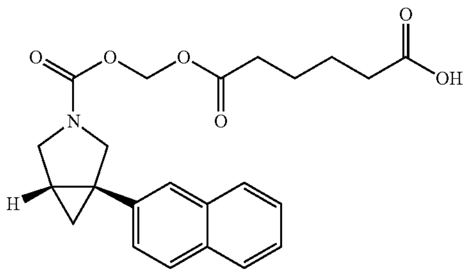 |

TABLE 6-continued
18 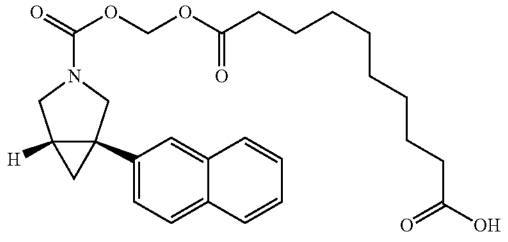 [SMILES: O=C(O)CCCCCCCCC(=O)OCOC(=O)N1C[C@H]2C[C@@]2(c2ccc3ccccc3c2)C1]
19 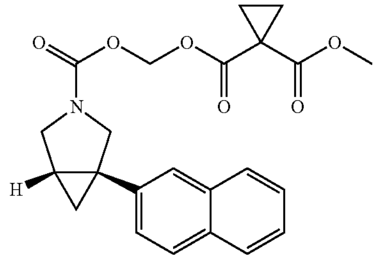 [SMILES: COC(=O)C1(C(=O)OCOC(=O)N2C[C@H]3C[C@@]3(c3ccc4ccccc4c3)C2)CC1]
20 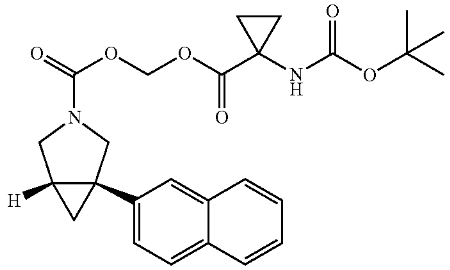 [SMILES: CC(C)(C)OC(=O)NC1(C(=O)OCOC(=O)N2C[C@H]3C[C@@]3(c3ccc4ccccc4c3)C2)CC1]
21 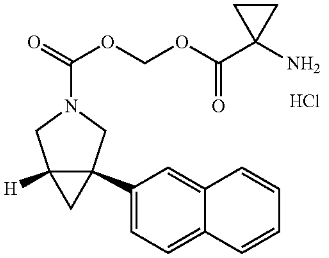 [SMILES: NC1(C(=O)OCOC(=O)N2C[C@H]3C[C@@]3(c3ccc4ccccc4c3)C2)CC1 ; Cl]
22 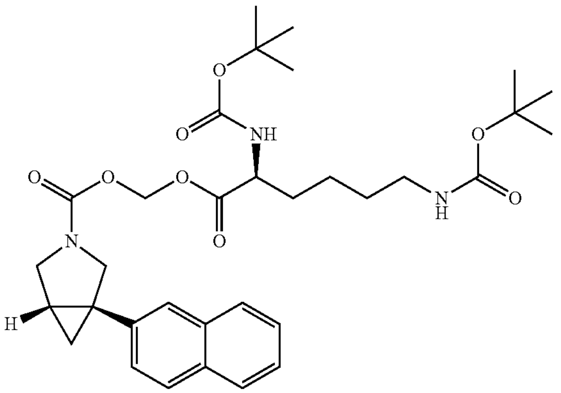 [SMILES: CC(C)(C)OC(=O)NCCCC[C@H](NC(=O)OC(C)(C)C)C(=O)OCOC(=O)N1C[C@H]2C[C@@]2(c2ccc3ccccc3c2)C1]

TABLE 6-continued
23
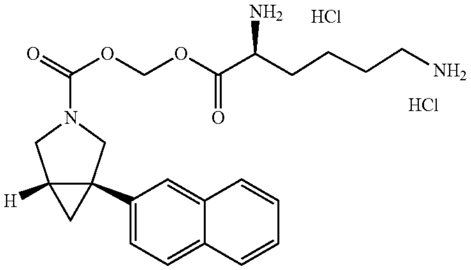 [SMILES: NCCCC[C@H](N)C(=O)OCOC(=O)N1C[C@H]2C[C@@]2(c2ccc3ccccc3c2)C1 ; Cl ; Cl]
24
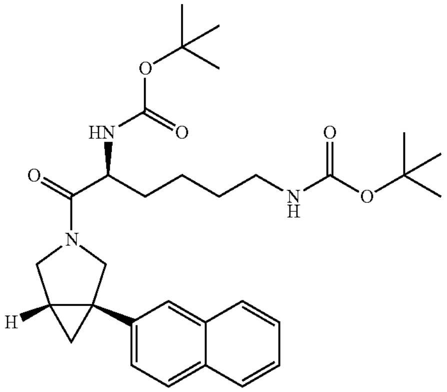 [SMILES: CC(C)(C)OC(=O)NCCCC[C@H](NC(=O)OC(C)(C)C)C(=O)N1C[C@H]2C[C@@]2(c2ccc3ccccc3c2)C1]
TABLE 7
25
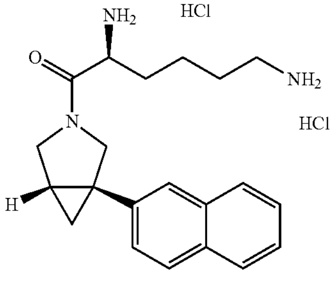 [SMILES: Cl ; NCCCC[C@H](N)C(=O)N1C[C@H]2C[C@@]2(c2ccc3ccccc3c2)C1 ; Cl]
26
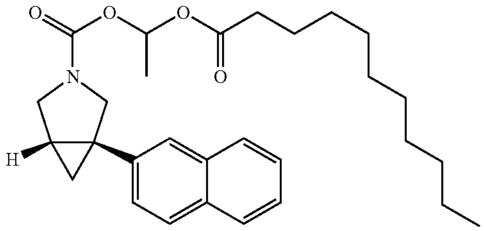 [SMILES: CCCCCCCCCCC(=O)OC(C)OC(=O)N1C[C@H]2C[C@@]2(c2ccc3ccccc3c2)C1]
27
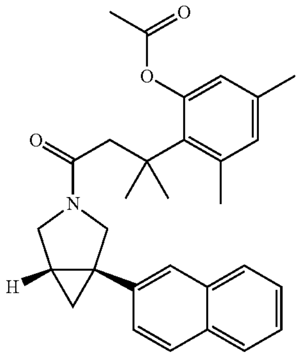 [SMILES: CC(=O)Oc1cc(C)cc(C)c1C(C)(C)CC(=O)N1C[C@H]2C[C@@]2(c2ccc3ccccc3c2)C1]
TABLE 7-continued
28
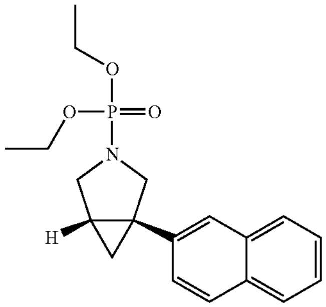 [SMILES: CCOP(=O)(OCC)N1C[C@H]2C[C@@]2(c2ccc3ccccc3c2)C1]
29
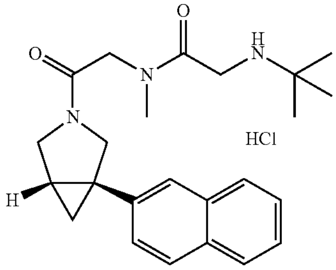 [SMILES: CN(CC(=O)N1C[C@H]2C[C@@]2(c2ccc3ccccc3c2)C1)C(=O)CNC(C)(C)C ; Cl]
30
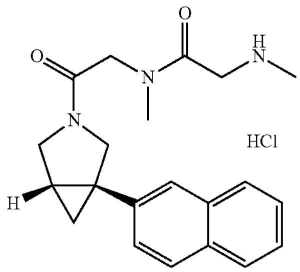 [SMILES: CNCC(=O)N(C)CC(=O)N1C[C@H]2C[C@@]2(c2ccc3ccccc3c2)C1 ; Cl]

TABLE 7-continued
31
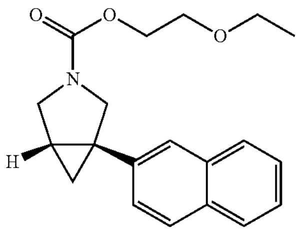 [SMILES: CCOCCOC(=O)N1C[C@H]2C[C@@]2(c2ccc3ccccc3c2)C1]
32
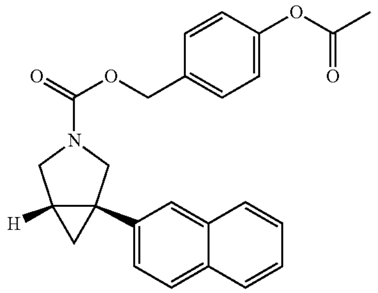 [SMILES: CC(=O)Oc1ccc(COC(=O)N2C[C@H]3C[C@@]3(c3ccc4ccccc4c3)C2)cc1]
33
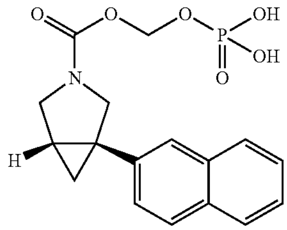 [SMILES: O=C(OCOP(=O)(O)O)N1C[C@H]2C[C@@]2(c2ccc3ccccc3c2)C1]
31
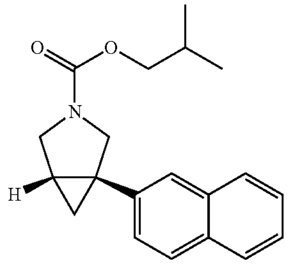 [SMILES: CC(C)COC(=O)N1C[C@H]2C[C@@]2(c2ccc3ccccc3c2)C1]
35
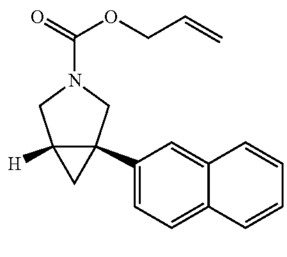 [SMILES: C=CCOC(=O)N1C[C@H]2C[C@@]2(c2ccc3ccccc3c2)C1]
36
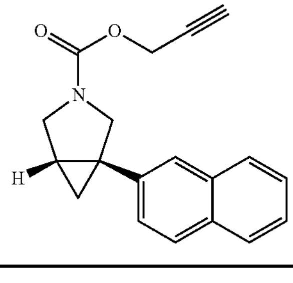
TABLE 8
37
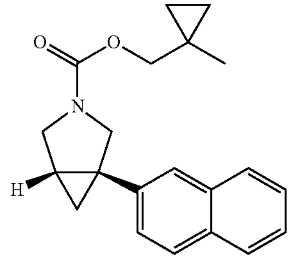 [SMILES: CC1(COC(=O)N2C[C@H]3C[C@@]3(c3ccc4ccccc4c3)C2)CC1]
38
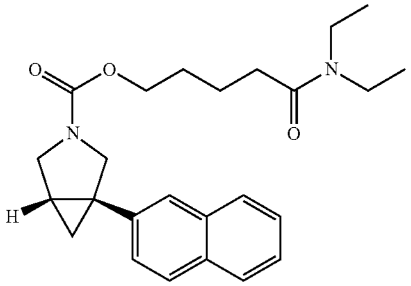 [SMILES: CCN(CC)C(=O)CCCCOC(=O)N1C[C@H]2C[C@@]2(c2ccc3ccccc3c2)C1]
39
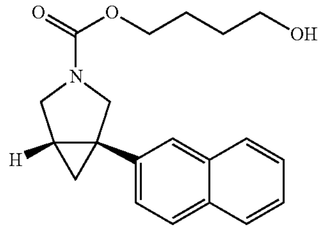 [SMILES: O=C(OCCCCO)N1C[C@H]2C[C@@]2(c2ccc3ccccc3c2)C1]
40
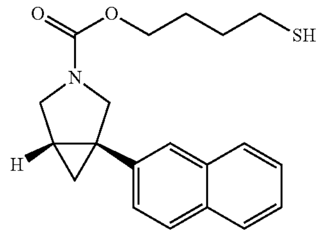 [SMILES: O=C(OCCCCS)N1C[C@H]2C[C@@]2(c2ccc3ccccc3c2)C1]
41
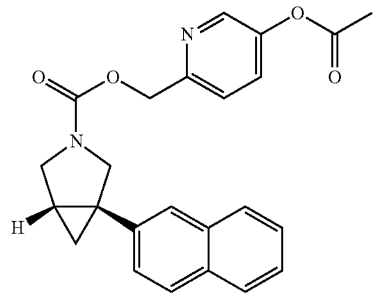 [SMILES: CC(=O)Oc1ccc(COC(=O)N2C[C@H]3C[C@@]3(c3ccc4ccccc4c3)C2)nc1]
42
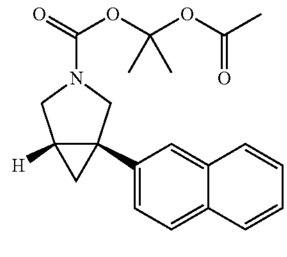 [SMILES: CC(=O)OC(C)(C)OC(=O)N1C[C@H]2C[C@@]2(c2ccc3ccccc3c2)C1]

TABLE 8-continued
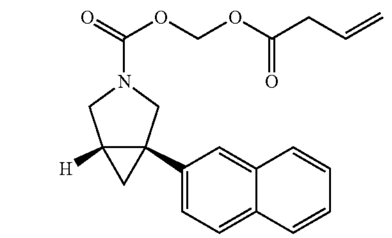 [SMILES: C=CCC(=O)OCOC(=O)N1C[C@H]2C[C@@]2(c2ccc3ccccc3c2)C1]
43
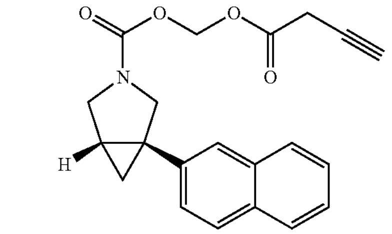 [SMILES: C#CCC(=O)OCOC(=O)N1C[C@H]2C[C@@]2(c2ccc3ccccc3c2)C1]
44
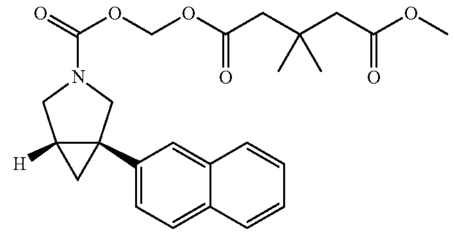 [SMILES: COC(=O)CC(C)(C)CC(=O)OCOC(=O)N1C[C@H]2C[C@@]2(c2ccc3ccccc3c2)C1]
45
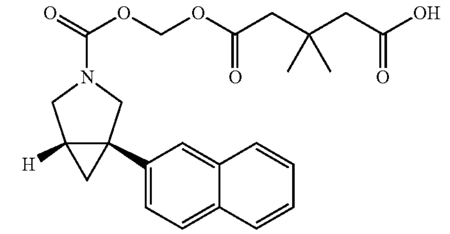 [SMILES: CC(C)(CC(=O)O)CC(=O)OCOC(=O)N1C[C@H]2C[C@@]2(c2ccc3ccccc3c2)C1]
46
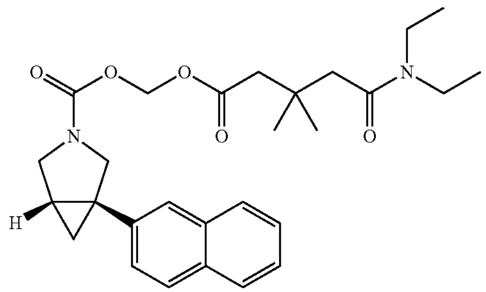 [SMILES: CCN(CC)C(=O)CC(C)(C)CC(=O)OCOC(=O)N1C[C@H]2C[C@@]2(c2ccc3ccccc3c2)C1]
47
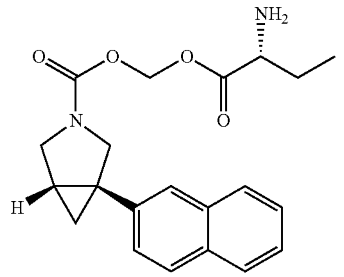 [SMILES: CC[C@@H](N)C(=O)OCOC(=O)N1C[C@H]2C[C@@]2(c2ccc3ccccc3c2)C1]
48
TABLE 9
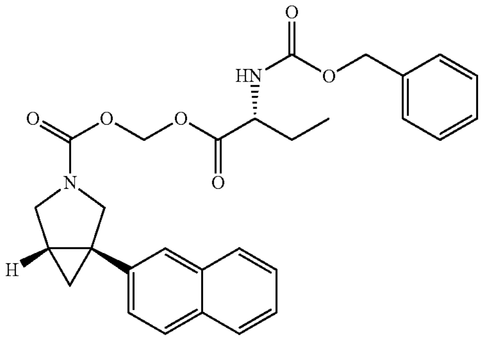 [SMILES: CC[C@@H](NC(=O)OCc1ccccc1)C(=O)OCOC(=O)N1C[C@H]2C[C@@]2(c2ccc3ccccc3c2)C1]
49
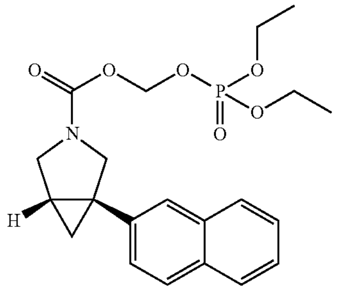 [SMILES: CCOP(=O)(OCC)OCOC(=O)N1C[C@H]2C[C@@]2(c2ccc3ccccc3c2)C1]
50
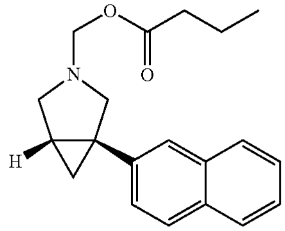 [SMILES: CCCC(=O)OCN1C[C@H]2C[C@@]2(c2ccc3ccccc3c2)C1]
51
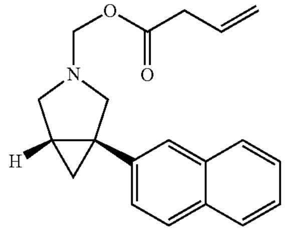 [SMILES: C=CCC(=O)OCN1C[C@H]2C[C@@]2(c2ccc3ccccc3c2)C1]
52
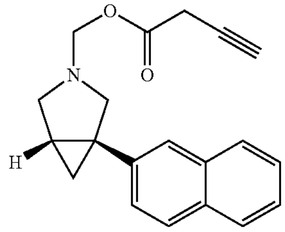 [SMILES: C#CCC(=O)OCN1C[C@H]2C[C@@]2(c2ccc3ccccc3c2)C1]
53
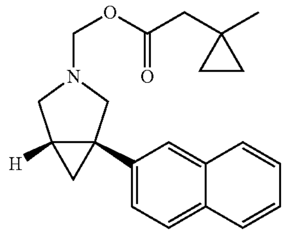 [SMILES: CC1(CC(=O)OCN2C[C@H]3C[C@@]3(c3ccc4ccccc4c3)C2)CC1]
54

TABLE 9-continued
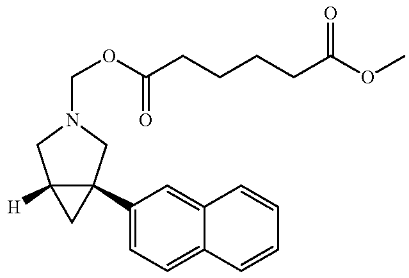 [SMILES: COC(=O)CCCCC(=O)OCN1C[C@H]2C[C@@]2(c2ccc3ccccc3c2)C1]
55
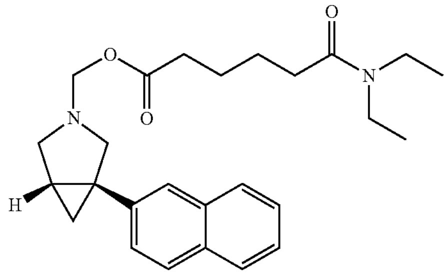 [SMILES: CCN(CC)C(=O)CCCCC(=O)OCN1C[C@H]2C[C@@]2(c2ccc3ccccc3c2)C1]
56
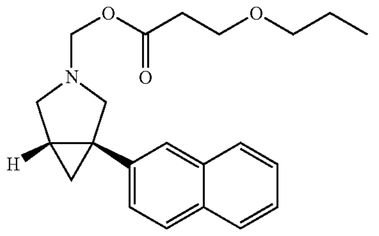 [SMILES: CCCOCCC(=O)OCN1C[C@H]2C[C@@]2(c2ccc3ccccc3c2)C1]
57
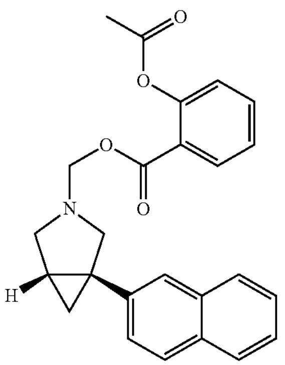 [SMILES: CC(=O)Oc1ccccc1C(=O)OCN1C[C@H]2C[C@@]2(c2ccc3ccccc3c2)C1]
58
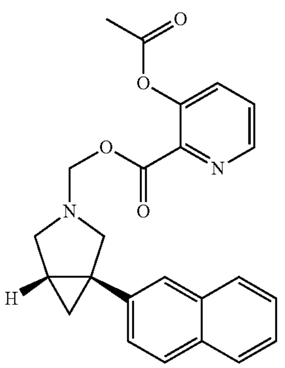 [SMILES: CC(=O)Oc1cccnc1C(=O)OCN1C[C@H]2C[C@@]2(c2ccc3ccccc3c2)C1]
59
TABLE 9-continued
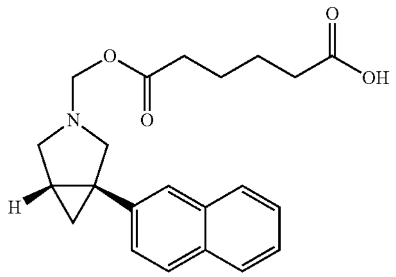 [SMILES: O=C(O)CCCCC(=O)OCN1C[C@H]2C[C@@]2(c2ccc3ccccc3c2)C1]
60
TABLE 10
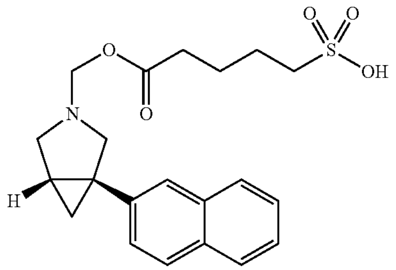 [SMILES: O=C(CCCCS(=O)(=O)O)OCN1C[C@H]2C[C@@]2(c2ccc3ccccc3c2)C1]
61
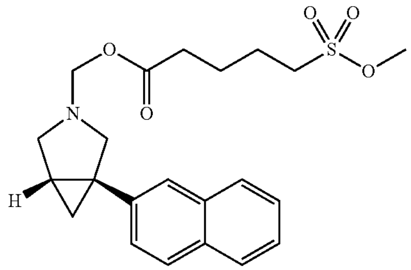 [SMILES: COS(=O)(=O)CCCCC(=O)OCN1C[C@H]2C[C@@]2(c2ccc3ccccc3c2)C1]
62
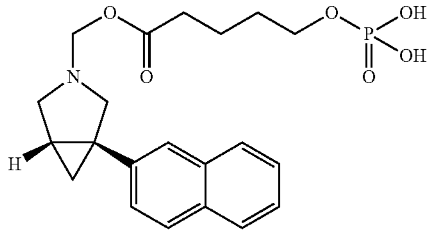 [SMILES: O=C(CCCCOP(=O)(O)O)OCN1C[C@H]2C[C@@]2(c2ccc3ccccc3c2)C1]
63
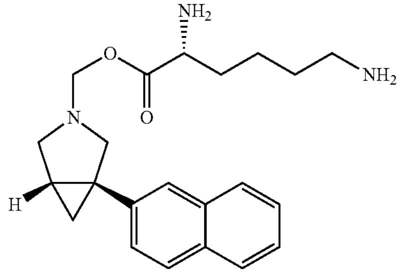 [SMILES: NCCCC[C@@H](N)C(=O)OCN1C[C@H]2C[C@@]2(c2ccc3ccccc3c2)C1]
64

TABLE 10-continued
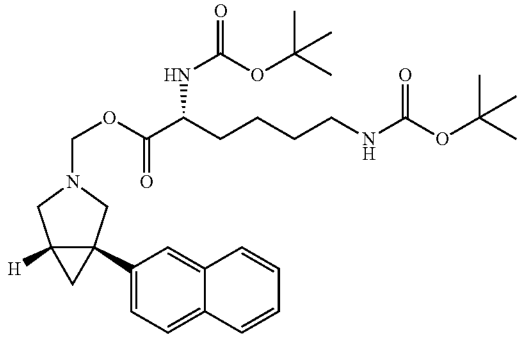 [SMILES: CC(C)(C)OC(=O)NCCCC[C@@H](NC(=O)OC(C)(C)C)C(=O)OCN1C[C@H]2C[C@@]2(c2ccc3ccccc3c2)C1]
65
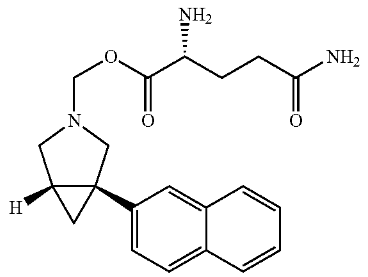 [SMILES: NC(=O)CC[C@@H](N)C(=O)OCN1C[C@H]2C[C@@]2(c2ccc3ccccc3c2)C1]
66
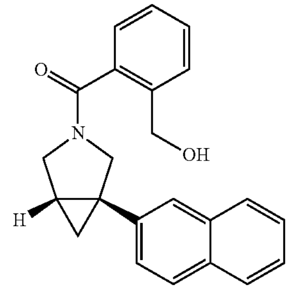 [SMILES: O=C(c1ccccc1CO)N1C[C@H]2C[C@@]2(c2ccc3ccccc3c2)C1]
67
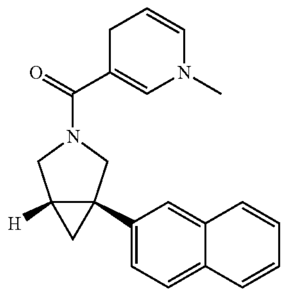 [SMILES: CN1C=CCC(C(=O)N2C[C@H]3C[C@@]3(c3ccc4ccccc4c3)C2)=C1]
68
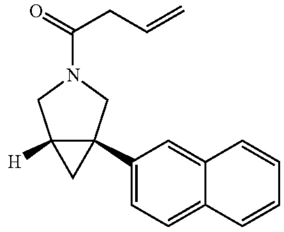 [SMILES: C=CCC(=O)N1C[C@H]2C[C@@]2(c2ccc3ccccc3c2)C1]
69
TABLE 10-continued
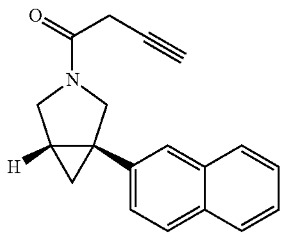 [SMILES: C#CCC(=O)N1C[C@H]2C[C@@]2(c2ccc3ccccc3c2)C1]
70
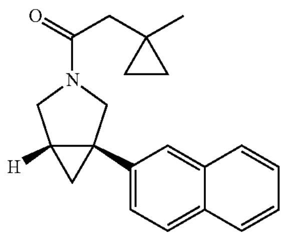 [SMILES: CC1(CC(=O)N2C[C@H]3C[C@@]3(c3ccc4ccccc4c3)C2)CC1]
71
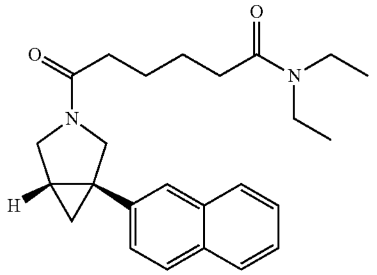 [SMILES: CCN(CC)C(=O)CCCCC(=O)N1C[C@H]2C[C@@]2(c2ccc3ccccc3c2)C1]
72
TABLE 11
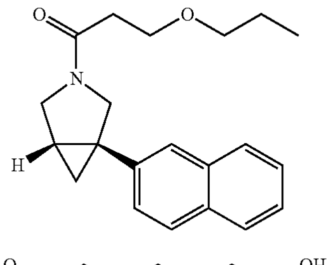
73
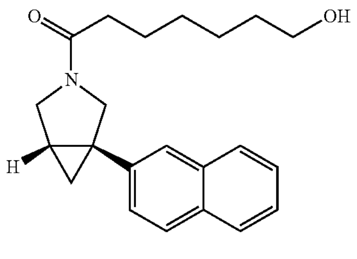 [SMILES: O=C(CCCCCCO)N1C[C@H]2C[C@@]2(c2ccc3ccccc3c2)C1]
74
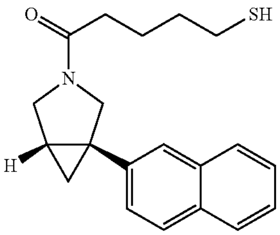 [SMILES: O=C(CCCCS)N1C[C@H]2C[C@@]2(c2ccc3ccccc3c2)C1]
75

TABLE 11-continued
76
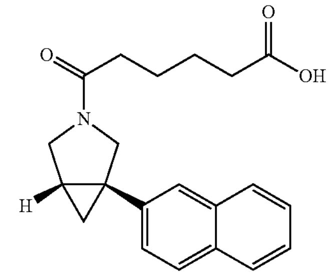 [SMILES: O=C(O)CCCCC(=O)N1C[C@H]2C[C@@]2(c2ccc3ccccc3c2)C1]
77
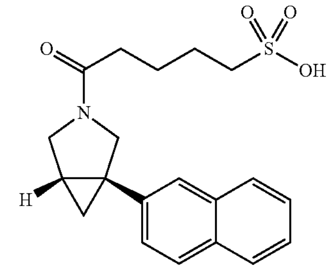 [SMILES: O=C(CCCCS(=O)(=O)O)N1C[C@H]2C[C@@]2(c2ccc3ccccc3c2)C1]
78
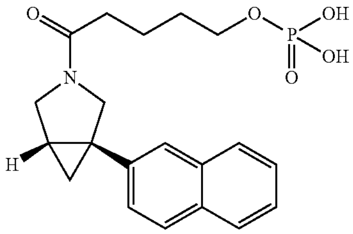 [SMILES: O=C(CCCCOP(=O)(O)O)N1C[C@H]2C[C@@]2(c2ccc3ccccc3c2)C1]
79
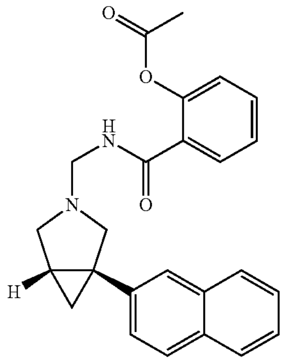 [SMILES: CC(=O)Oc1ccccc1C(=O)NCN1C[C@H]2C[C@@]2(c2ccc3ccccc3c2)C1]
80
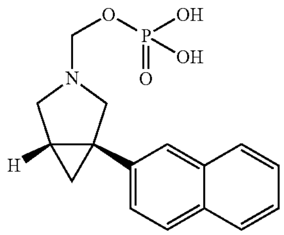 [SMILES: O=P(O)(O)OCN1C[C@H]2C[C@@]2(c2ccc3ccccc3c2)C1]
81
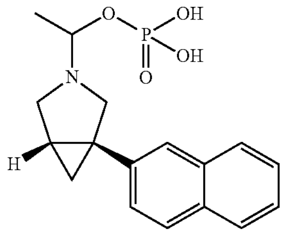 [SMILES: CC(OP(=O)(O)O)N1C[C@H]2C[C@@]2(c2ccc3ccccc3c2)C1]
TABLE 11-continued
82
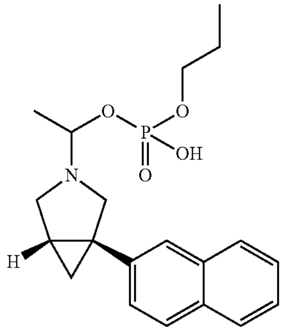 [SMILES: CCCOP(=O)(O)OC(C)N1C[C@H]2C[C@@]2(c2ccc3ccccc3c2)C1]
83
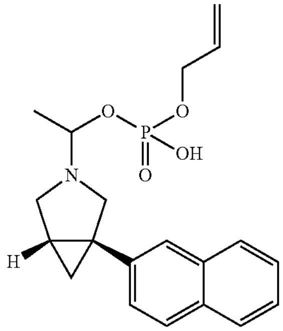 [SMILES: C=CCOP(=O)(O)OC(C)N1C[C@H]2C[C@@]2(c2ccc3ccccc3c2)C1]
84
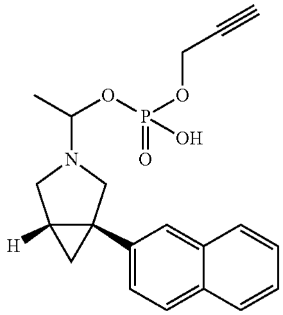 [SMILES: C#CCOP(=O)(O)OC(C)N1C[C@H]2C[C@@]2(c2ccc3ccccc3c2)C1]
TABLE 12
85
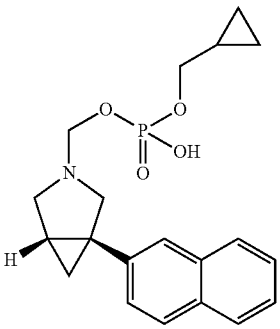 [SMILES: O=P(O)(OCC1CC1)OCN1C[C@H]2C[C@@]2(c2ccc3ccccc3c2)C1]

TABLE 12-continued
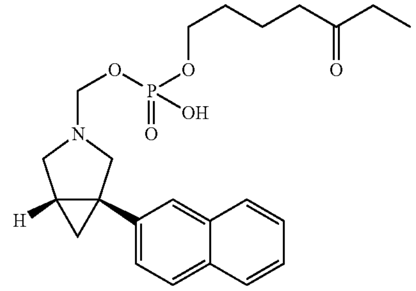 [SMILES: CCC(=O)CCCCOP(=O)(O)OCN1C[C@H]2C[C@@]2(c2ccc3ccccc3c2)C1]
86
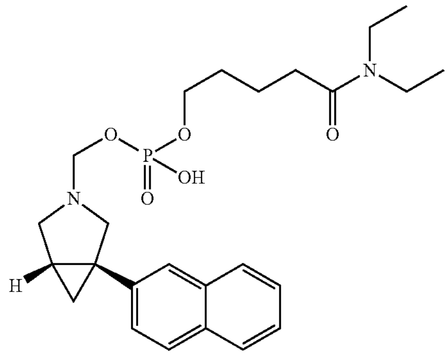 [SMILES: CCN(CC)C(=O)CCCCOP(=O)(O)OCN1C[C@H]2C[C@@]2(c2ccc3ccccc3c2)C1]
87
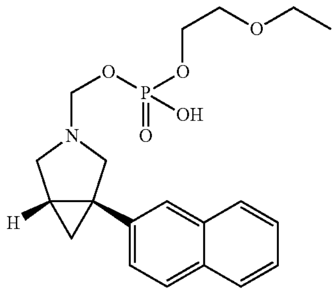 [SMILES: CCOCCOP(=O)(O)OCN1C[C@H]2C[C@@]2(c2ccc3ccccc3c2)C1]
88
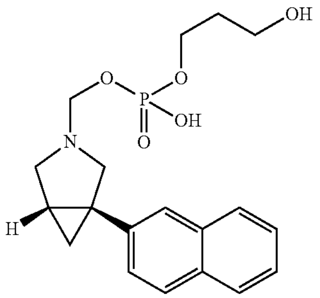
89
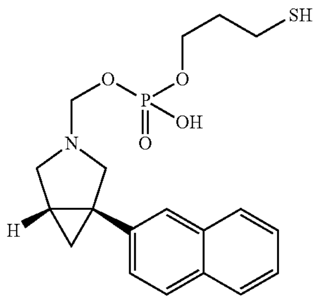 [SMILES: O=P(O)(OCCCO)OCN1C[C@H]2C[C@@]2(c2ccc3ccccc3c2)C1]
90
TABLE 12-continued
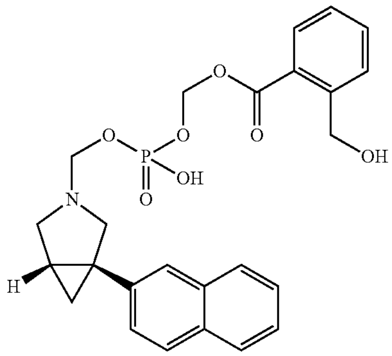 [SMILES: O=C(OCOP(=O)(O)OCN1C[C@H]2C[C@@]2(c2ccc3ccccc3c2)C1)c1ccccc1CO]
91
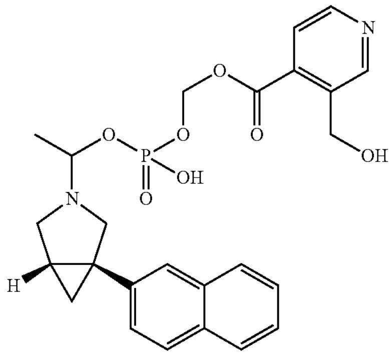 [SMILES: CC(OP(=O)(O)OCOC(=O)c1ccncc1CO)N1C[C@H]2C[C@@]2(c2ccc3ccccc3c2)C1]
92
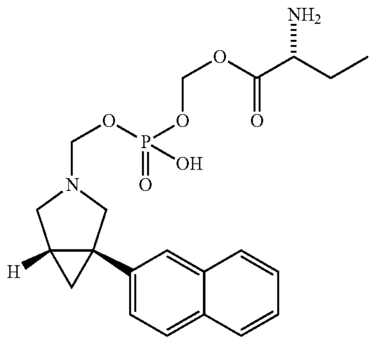
93
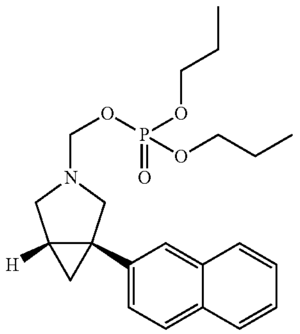 [SMILES: CCCOP(=O)(OCCC)OCN1C[C@H]2C[C@@]2(c2ccc3ccccc3c2)C1]
94

TABLE 13
95
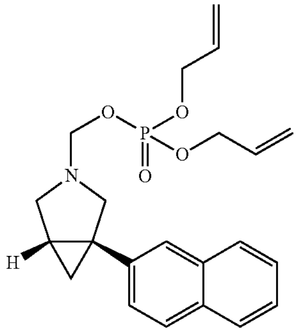 [SMILES: C=CCOP(=O)(OCC=C)OCN1C[C@H]2C[C@@]2(c2ccc3ccccc3c2)C1]
96
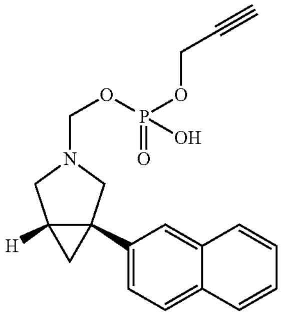 [SMILES: C#CCOP(=O)(O)OCN1C[C@H]2C[C@@]2(c2ccc3ccccc3c2)C1]
97
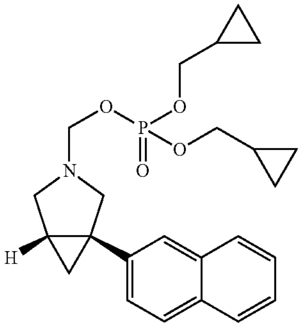 [SMILES: O=P(OCC1CC1)(OCC1CC1)OCN1C[C@H]2C[C@@]2(c2ccc3ccccc3c2)C1]
98
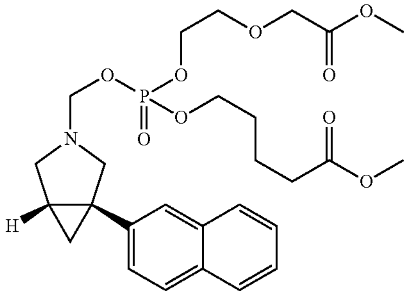 [SMILES: COC(=O)CCCCOP(=O)(OCCOCC(=O)OC)OCN1C[C@H]2C[C@@]2(c2ccc3ccccc3c2)C1]
99
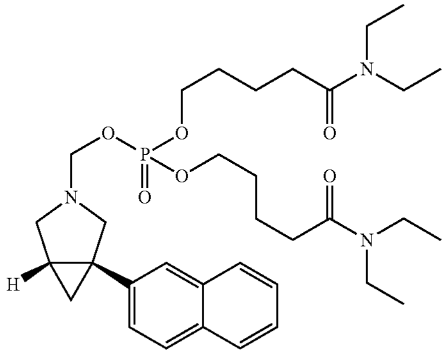 [SMILES: CCN(CC)C(=O)CCCCOP(=O)(OCCCCC(=O)N(CC)CC)OCN1C[C@H]2C[C@@]2(c2ccc3ccccc3c2)C1]
TABLE 13-continued
100
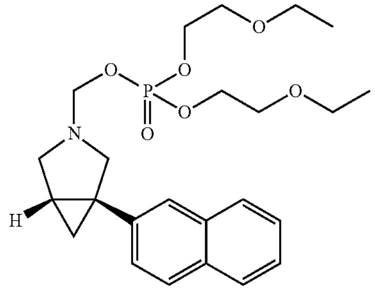 [SMILES: CCOCCOP(=O)(OCCOCC)OCN1C[C@H]2C[C@@]2(c2ccc3ccccc3c2)C1]
101
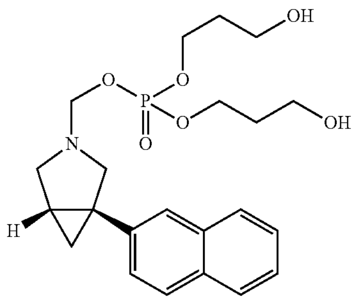
102
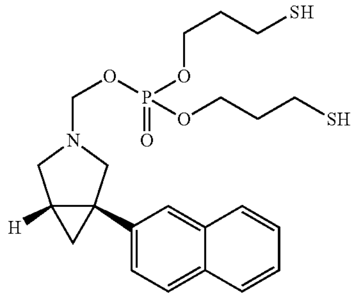 [SMILES: O=P(OCCCO)(OCCCO)OCN1C[C@H]2C[C@@]2(c2ccc3ccccc3c2)C1]
103
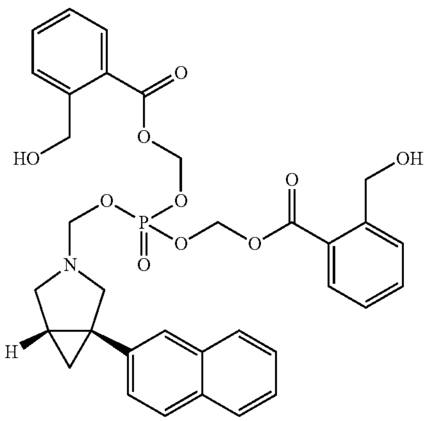 [SMILES: O=C(OCOP(=O)(OCOC(=O)c1ccccc1CO)OCN1C[C@H]2C[C@@]2(c2ccc3ccccc3c2)C1)c1ccccc1CO]

TABLE 13-continued
104
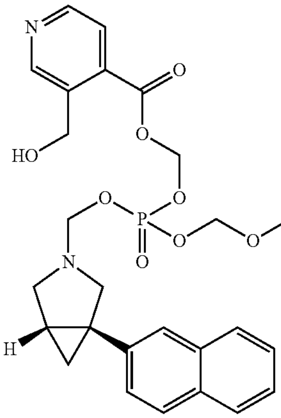
TABLE 14
105
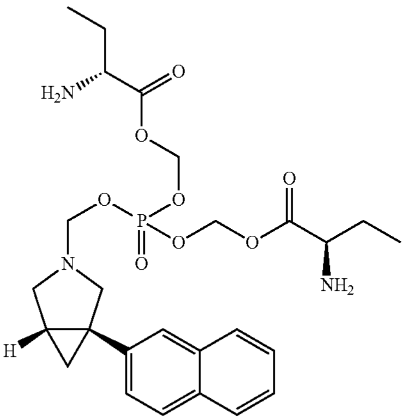 [SMILES: CC[C@@H](N)C(=O)OCOP(=O)(OCOC(=O)[C@H](N)CC)OCN1C[C@H]2C[C@@]2(c2ccc3ccccc3c2)C1]
106
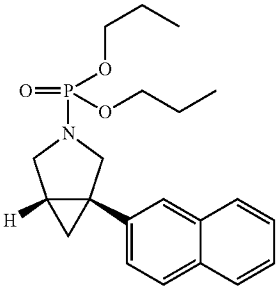 [SMILES: CCCOP(=O)(OCCC)N1C[C@H]2C[C@@]2(c2ccc3ccccc3c2)C1]
107
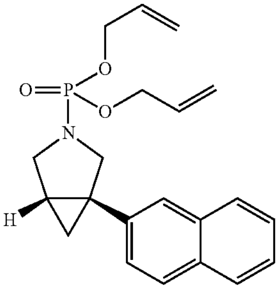 [SMILES: C=CCOP(=O)(OCC=C)N1C[C@H]2C[C@@]2(c2ccc3ccccc3c2)C1]
TABLE 14-continued
108
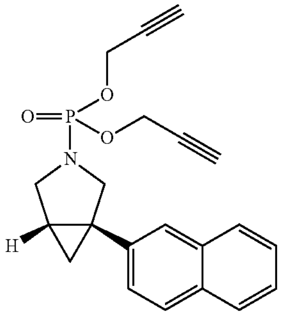 [SMILES: C#CCOP(=O)(OCC#C)N1C[C@H]2C[C@@]2(c2ccc3ccccc3c2)C1]
109
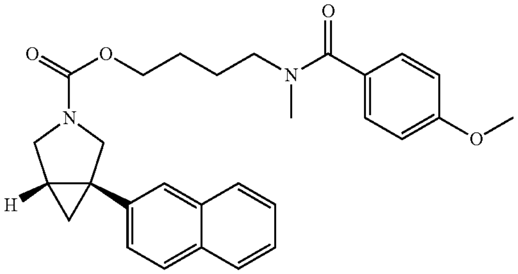 [SMILES: COc1ccc(C(=O)N(C)CCCCOC(=O)N2C[C@H]3C[C@@]3(c3ccc4ccccc4c3)C2)cc1]
110
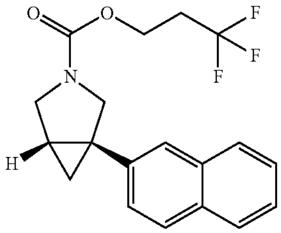 [SMILES: O=C(OCCC(F)(F)F)N1C[C@H]2C[C@@]2(c2ccc3ccccc3c2)C1]
111
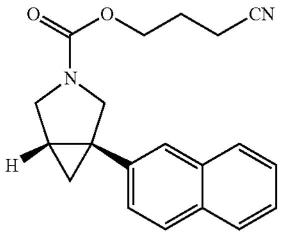 [SMILES: N#CCCCOC(=O)N1C[C@H]2C[C@@]2(c2ccc3ccccc3c2)C1]
112
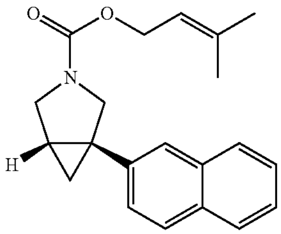 [SMILES: CC(C)=CCOC(=O)N1C[C@H]2C[C@@]2(c2ccc3ccccc3c2)C1]
113
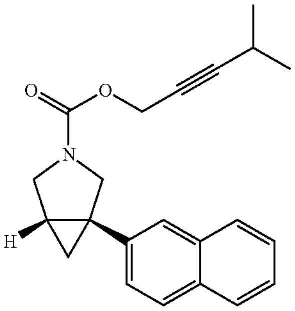 [SMILES: CC(C)C#CCOC(=O)N1C[C@H]2C[C@@]2(c2ccc3ccccc3c2)C1]

TABLE 14-continued

| | |
|---|---|
| 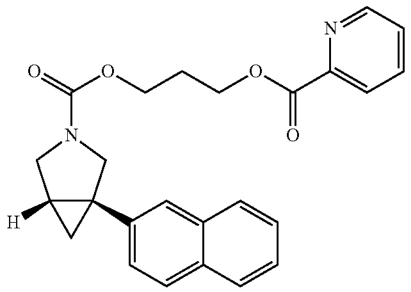 | 114 |

TABLE 15

| EX | Prop | Data |
|---|---|---|
| 1 | 1 | NMR2; δ: 0.87-0.92 (m, 1 H), 0.99 (t, J = 7.4 Hz, 1 H), 1.23-1.26 (m, 1 H), 1.70 (q, J = 7.4 Hz, 2 H), 1.97-2.05 (m, 1 H), 2.20-2.32 (m, 2 H), 3.58-3.81 (m, 2 H), 3.85-4.36 (m, 2 H), 7.24-7.27 (m, 1 H), 7.43-7.49 (m, 2 H) 7.66 (s, 1 H) 7.75-7.82 (m, 3 H). |
| 2 | 1 | MS; [M]' = 321 |
| 3 | 1 | MS; [M]' = 363 |
| 4 | 1 | MS; [M]' = 351 |
| 5 | 5 | NMR2; δ: 0.93 (t, J = 4.4 Hz, 1 H), 1.19-1.24 (m, 1 H), 1.28 (t, J = 7.1 Hz, 3 H), 1.96 (t, J = 3.9 Hz, 1 H), 3.55-3.85 (m, 3 H), 4.01-4.20 (m, 3 H), 7.25-7.28 (m, 1 H), 7.40-7.50 (m, 2 H) 7.64 (s, 1 H) 7.76-7.82 (m, 3 H) |
| 6 | 5 | MS; [M]' = 323 |
| 7 | 5 | MS; [M]' = 365 |
| 8 | 8 | NMR2; δ: 0.93 (t, J = 4.4 Hz, 1 H), 1.22-1.26 (m, 1 H), 1.96-2.01 (m, 1 H), 2.13 (s, 3 H), 3.36-3.87 (m, 3 H), 4.05-4.15 (m, 3 H), 5.78 (s, 2 H), 7.23-7.26 (m, 1 H), 7.44-7.50 (m, 2 H) 7.63 (s, 1 H) 7.76-7.80 (m, 3 H) |
| 9 | 8 | MS; [M]' = 381 |
| 10 | 8 | MS; [M + H]' = 452 |
| 11 | 8 | MS; [M + H]' = 508 |
| 12 | 8 | MS; [M]' = 425 |
| 13 | 8 | MS; [M + H]' = 482 |
| 14 | 8 | MS; [M]' = 501 |
| 15 | 8 | MS; [M]' = 531 |
| 16 | 8 | MS; [M + H]' = 588 |
| 17 | 17 | NMR2; 0.92 (t, J = 4.6 Hz, 1 H), 1.23-1.27 (m, 1 H), 1.60-1.80 (m, 4 H), 1.90-1.99 (m, 1 H), 2.33-2.42 (m, 4 H), 3.65-3.85 (m, 3 H), 4.05-4.15 (m, 1 H), 5.79 (s, 2 H), 7.22-7.26 (m, 1 H), 7.43-7.48 (m, 2 H), 7.63 (s, 1 H) 7.77-7.80 (m, 3 H) |
| 18 | 17 | MS; [M]' = 467 |
| 19 | 8 | MS; [M + H]' = 410 |
| 20 | 8 | MS; [M + Na]' = 489 |

TABLE 16

| EX | Prop | Data |
|---|---|---|
| 21 | 21 | NMR2; 0.93 (t, J = 4.6 Hz, 1 H), 1 20-1.26 (m, 1 H), 1.62 (s, 2 H), 1.77 (s, 2 H), 3.60-3.82 (m, 3 H), 4.04 (t, J = 10.4 Hz, 1 H), 5.82 (br-s, 2 H), 7.20-7.25 (m, 1 H), 7.41-7.48 (m, 2 H) 7.61 (d, J = 15.5 Hz, 1 H), 7.74-7.78 (m, 3 H) |
| 22 | 8 | MS; [M + Na]' = 634 |
| 23 | 21 | MS; [M + Na]' = 434 |
| 24 | 24 | MS; [M]' = 537 |
| 25 | 21 | MS; [M]' = 337 |
| 26 | 8 | MS; [M + Na]' = 466 |
| 27 | 27 | NMR2; 0.74(1H, dd, J = 5.0 Hz, 9.8 Hz), 1.11-1.19(1H, m), 1.57-1.66(6H, m), 1.87-1.98(1H, m), 2.19-2.34(6H, m), 2.54-2.60(3H, m), 2.71-2.85(2H, m), 3.46-3.64(2H, m), 3.64-4.28(2H, m), 6.58-6.63(1H, m), 6.80-6.84(1H, m), 7.16-7.22(1H, m), 7.4-7.51(2H, |

TABLE 16-continued

| EX | Prop | Data |
|---|---|---|
| | | m), 7.57(1H, dd, J = 1.5 Hz, 17.4 Hz), 7.72-7.83(3H, m). |
| 28 | 28 | NMR2; 1.09(1H, dd, J = 4.9 Hz, 7.9 Hz), 1.15(1H, dd, J = 4.6 Hz, 4.6 Hz), 1.30-1.38(6H, m), 1.87-1.95(1H, m), 3.44-3.54(2H, m), 3.58(1H, dd, J = 3.1 Hz, 9.5 Hz), 3.78(1H, dd, J = 2.8 Hz, 9.5 Hz), 4.01-4.16(4H, m), 7.23-7.29(1H, m), 7.40-7.50(2H, m), 7.61-7.66(1H, m), 7.74-7.83(3H, m). |
| 29 | 29 | NMR1; 0.84-0.92(1H, m), 0.95-1.11(9H, m), 1.20-1.30(1H, m), 2.08-2.26(1H, m), 2.84-3.16(3H, m) 3.28-4.00(5H, m), 4.10-4.20(1H, m), 4.20-4.31(1H, m), 4.44-4.70(1H, m), 7.33-7.42(1H, m), 7.44-7.55(2H, m), 7.76-7.83(1H, m), 7.83-7.94(3H, m), 7.96-8.20(2H, br). |
| 30 | 29 | NMR1; 0.83-0.98(1H, m), 1.20-1.33(1H, m), 2.08-2.30(1H, m), 2.52-2.61(3H, m), 2.85-2.99(3H, m), 3.38-3.87(4H, m), 3.89-4.42(4H, m), 7.33-7.41(1H, m), 7.43-7.55(2H, m), 7.76-7.82(1H, m), 7.83-7.93(3H, m), 8.71-8.94(2H, br). |

TEST EXAMPLE

Test Example 1: Confirmatory Test for Conversion to (1R,5S)-1-(naphthalen-2-yl)-3-azabicyclo[3.1.0]hexane (1) In Vitro Metabolic Reaction The reaction system described below was prepared, and the conversion of a test compound to (1R,5S)-1-(naphthalen-2-yl)-3-azabicyclo[3.1.0]hexane was evaluated in the 9000 g supernatant fraction (89) of human liver and in a buffer.

Human liver S9 was purchased from Sekisul XenoTech and used. The test compound was dissolved in DMSO to 10 mM and further diluted with acetonitrile to 100 μM, The solution of the test compound was prepared at the time of use.

<Reaction System> Final Concentration

Test compound 1 μM

Human liver S9 1 mg/mL

Coenzyme (NADPH/NADH) 1 MM each

Magnesium chloride 5 mM 100 mM Phosphate buffer (pH 7.4)

Number of cases: n=2

<Reaction Method>

The reaction system without the test compound was preincubated at 37° C. for 5 min, and then the reaction was started by adding the test compound solution. After the addition of the coenzyme, the reaction was stopped by adding acetonitrile solution containing the internal standard at each predetermined time. The reaction mixture was used as a sample for assay. In addition, samples for calibration curve (0.01, 0.1, 1 μM) were prepared with the same composition.

(2) Analysis Method

Samples for assay and calibration were centrifuged, and the supernatant was injected into a liquid chromatograph-tandem mass spectrometer to measure (1R,5S)-1-(naphthalen-2-yl)-3-azabicyclo[3.1.0]hexane in the reaction system. Ionization was performed by electrospray ionization (ESI) method with cationic detection, and a selective reaction detection method using set precursor and product ions was used.

(3) Data Analysis

For the conversion of the test compound to (1R,5S)-1-(naphthalen-2-yl)-3-azabicyclo[3.1.0]hexane, the reaction samples at 0 minute and at 60 minutes were compared. Those that satisfied all of the following criteria were judged as "conversion of the test compound to (1R,5S)-1-(naphthalen-2-yl)-3-azabicyclo[3.1.0]hexane".

In the reaction system using human liver S9, the formation of (1R,5S)-1-(naphthalen-2-yl)-3-azabicyclo[3.1.0]hexane was not observed in the 0-minute reaction sample, but was observed in the 60-minute reaction sample.

In the reaction system using buffer, no formation of (1R,5S)-1-(naphthalen-2-yl)-3-azabicyclo[3.1.0]hexane was observed in the 0-minute and 60-minute reaction samples.

The test results are shown Tables below.

The concentration (μM) of (1R,5S)-1-(naphthalen-2-yl)-3-azabicyclo[3.1.0]hexane formed is the mean value for n=2.

TABLE 17

| EX | Concentration (μM) of (1R, 5S)-1-(naphthalen-2-yl)-3-azabicyclo[3.1.0]hexane formed |
|---|---|
| 5 | 0.07 |
| 8 | 0.42 |
| 9 | 0.49 |
| 10 | 0.19 |
| 11 | 0.12 |
| 12 | 0.47 |
| 13 | 0.21 |
| 14 | 0.21 |
| 15 | 0.22 |
| 16 | 0.20 |
| 17 | 0.32 |
| 18 | 0.18 |
| 19 | 0.39 |
| 20 | 0.14 |
| 21 | 0.21 |
| 22 | 0.14 |
| 26 | 0.17 |
| 27 | 0.25 |

INDUSTRIAL AVAILABILITY

This compound of Formula [I] is chemically or enzymatically converted to (1R,5S)-1-(naphthalen-2-yl)-3-azabicyclo[3.1.0]hexane under physiological conditions and is useful in the treatment or prevention of central nervous system (CNS) disorders.

The invention claimed is:

1. A compound represented by Formula [I]:

[I]

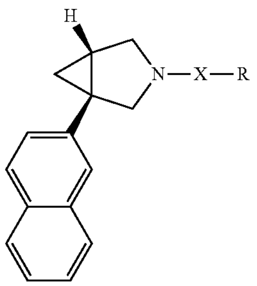

wherein

X is

1) —C(═O)—O—,

2) —C(═O)—O—C($X^{11a}$)($X^{12a}$)—O—C(═O)—,

3) —C(═O)—O—C($X^{11b}$)($X^{12b}$)—O—P(═O)(—O$R^{2b}$)—O—,

4) —C(═O)—,

5) —C(═O)—C($X^{11c}$)($X^{12c}$)—N($X^{13c}$)—C(═O)—,

6) —C($X^{11d}$)($X^{12d}$)—O—C(═O)—,

7) —C($X^{11e}$)($X^{12e}$)—N($X^{13e}$)—C(═O)—,

8) —C($X^{11f}$)($X^{12f}$)—O—P(═O)(—O$R^{2f}$)—O—,

9) —C($X^{11g}$)($X^{12g}$)—O—P(═O)(—O$R^{2g}$)—O—C($X^{11h}$)($X^{12h}$)—O—C(═O)—, or

10) —P(═O)(—O$R^{2i}$)—O—;

$X^{11a}$, $X^{11b}$, $X^{11c}$, $X^{11d}$, $X^{11e}$, $X^{11f}$, $X^{11g}$, $X^{11h}$, $X^{12a}$, $X^{12b}X^{12c}$, $X^{12d}$, $X^{12e}$, $X^{12f}$, $X^{12g}$, and $X^{12h}$ are independently H or an optionally substituted $C_1$-$C_6$ alkyl, or $X^{11a}$ and $X^{12a}$, $X^{11b}$ and $X^{12b}$, $X^{11c}$ and $X^{12c}$, $X^{11d}$ and $X^{12d}$, $X^{11e}$ and $X^{12e}$, $X^{11f}$ and $X^{12f}$, $X^{11g}$ and $X^{12g}$, and, $X^{11h}$ and $X^{12h}$ each may be taken together with a carbon atom to which they are both bonded to form a $C_3$-$C_6$ cycloalkane ring or a 3- to 6-membered heterocycloalkane ring;

$X^{13c}$ and $X^{13e}$ are independently H or an optionally substituted $C_1$-$C_6$ alkyl;

R, $R^{2b}$, $R^{2f}$, $R^{2g}$ and $R^{2i}$ are independently i) H, ii) an optionally substituted $C_1$-$C_{18}$ alkyl, iii) an optionally substituted $C_2$-$C_6$ alkenyl, iv) an optionally substituted $C_2$-$C_6$ alkynyl, v) an optionally substituted $C_3$- to $C_6$-cycloaryl, vi) an optionally substituted 6- to 10-membered aryl, or vii) an optionally substituted 5- to 10-membered heterocyclic ring group;

wherein when R, $R^{2b}$, $R^{2f}$, $R^{2g}$ and $R^{2i}$ are substituted, each is optionally substituted by 1 to 3, same or different groups independently selected from the group consisting of the following:

1) a $C_1$-$C_6$ alkyl, 2) a hydroxy $C_1$-$C_6$ alkyl, 3) a $C_3$-$C_6$ cycloalkyl optionally substituted by 1 to 3, same or different $C_1$-$C_6$ alkyl, 4) —C(═O)—O—$R^{11a}$, 5) —O—C(═O)—$R^{11b}$, 6) —C(═O)—N($R^{12a}$)—$R^{13a}$, 7) —N($R^{12b}$)—C(═O)—$R^{13b}$, 8) —N($R^{12c}$)—C(═O)—O—$R^{20}$,

9) —S$R^{14}$,

10) —O$R^{15}$,

11) —N($R^{12d}$)—$R^{16}$,

12) —S(═O)(═O)—O$R^{17}$,

13) —O—P(═O)(O$R^{18}$)—O$R^{19}$, 14) an optionally substituted 6- to 14-membered aryl, wherein the optionally substituted 6- to 10-membered aryl is a 6- to 10-membered aryl optionally by substituted by 1 to 3, same or different groups selected from the group consisting of a $C_1$-$C_6$ alkyl, a hydroxy $C_1$-$C_6$ alkyl and a $C_1$-$C_6$ alkanoyloxy, 15) an optionally substituted 5- to 10-membered heterocyclic ring group, wherein the optionally substituted 5- to 10-membered heterocyclic ring group is a 5- to 10-membered heterocyclic ring group optionally substituted by 1 to 3, same or different groups selected from the group consisting of a $C_1$-$C_6$ alkanoyloxy, 16) a halogen, and 17) cyano, $R^{11a}$, $R^{11b}$, $R^{12a}$, $R^{12b}$, $R^{12c}$, $R^{12d}$, $R^{13a}$, $R^{13b}$, $R^{14}$, $R^{15}$, $R^{16}$, $R^{17}$, $R^{18}$, $R^{19}$, and $R^{20}$ are independently H, an optionally substituted $C_1$-$C_6$ alkyl, an optionally substituted C 1- to C6-membered heterary1, wherein the optionally substituted $C_1$-$C_6$ alkyl is optionally substituted by 1 to 2, same or different groups selected from the group consisting of an optionally substituted phenyl and amino, the optionally substituted 6- to 10-membered aryl is optionally substituted substituted by 1 to 3, same or different groups selected from the group consisting of hydroxy $C_1$-$C_6$ alkyl and a $C_1$-$C_6$ alkoxy, the optionally substituted 5- to 10-membered heteroaryl is optionally substituted by 1 to 3, same or different hydroxy $C_1$-$C_6$ alkyl, or a salt thereof.

2. The compound or salt thereof according to claim 1, wherein X is

—C(═O)—O—,

—C(═O)—O—C($X^{11a}$)($X^{12a}$)—O—C(═O)—,

—C(═O)—,

—C(═O)—C($X^{11c}$)($X^{12c}$)—N($X^{13c}$)—C(═O)—, or

—P(═O)(—$OR^{2i}$)—O—;

$X^{11a}$, $X^{11c}$, $X^{12a}$ and $X^{12c}$ are independently H or $C_1$-$C_6$ alkyl;

$X^{13c}$ is $C_1$-$C_6$ alkyl;

R and $R^{2i}$ are independently an optionally substituted $C_1$-$C_{18}$ alkyl, or an optionally substituted $C_3$-$C_6$ cycloalkyl, wherein when R and $R^{2i}$ are substituted, they are optionally substituted by 1 or 2, same or different groups selected from the group consisting of —C(═O)—O—$R^{11a}$, —NH—C(═O)—O—$R^{20}$, —NH—$R^{16}$, and an optionally substituted 6- to 10-membered aryl, wherein the optionally substituted 6- to 10-membered aryl is optionally substituted by 1 to 3, same or different groups selected from the group consisting of a $C_1$-$C_6$ alkyl and a $C_1$-$C_6$ alkanoyloxy;

$R^{11a}$ is H, or an optionally substituted $C_1$-$C_6$ alkyl, wherein the optionally substituted $C_1$-$C_6$ alkyl is optionally substituted by a phenyl optionally substituted by 1 to 3, same or different $C_1$-$C_6$ alkoxy;

$R^{16}$ is H, or a $C_1$-$C_6$ alkyl;

$R^{20}$ is a $C_1$-$C_6$ alkyl.

3. The compound or salt thereof according to claim 2, wherein X is —C(═O)—O—, —C(═O)—O—C($X^{11a}$)($X^{12a}$)—O—C(═O)—, or —C(═O)—;

$X^{11a}$ and $X^{12a}$ are independently H or methyl.

4. A pharmaceutical composition comprising the compound or salt thereof according to claim 1, and a pharmaceutically acceptable carrier.

5. A method for treating a central nervous system (CNS) disorder, comprising administering to a subject a thereapeutically effective amount of the pharmaceutical composition according to claim 4.

6. A method for treating a central nervous system (CNS) disorder, comprising administering to a subject a therapeutically effective amount of the compound or salt thereof according to claim 1.

7. A medicament for treating a central nervous system (CNS) disorder, comprising the compound or salt thereof according to claim 1.

8. A compound represented by Formula [I]:

[I]

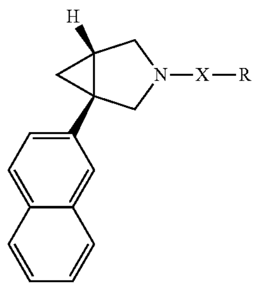

wherein

X is

1) —C(═O)—O—,

2) —C(═O)—O—C($X^{11a}$)($X^{12a}$)—O—C(═O)—,

3) —C(═O)—C—C($X^{11b}$)($X^{12b}$)—O—P(═O)(—$OR^{2b}$)—O—,

5) —C(═O)—C($X^{12c}$)—N($X^{13c}$)—C(═O)—,

6) —C($X^{11d}$)($X^{12d}$)—O—C(═O)—,

7) —C($X^{11e}$)($X^{12e}$)—C—(═O)—,

8) —C($X^{11f}$)($X^{12f}$)—O—P(═O)(—$OR^{2f}$)—O—,

9) —C($X^{11g}$)($X^{12g}$)—O—P(═O)(—$OR^{2g}$)—O—C($X^{11h}$)($X^{12h}$)—O—C(═O)—, or

10) —P(═O)(—$OR^{2i}$)—O—;

$X^{11a}$, $X^{11b}$, $X^{11c}$, $X^{11d}$, $X^{11e}$, $X^{11f}$, $X^{11g}$, $X^{11h}$, $X^{12a}$, $X^{12b}X^{12c}$, $X^{12d}$, $X^{12e}$, $X^{12f}$, $X^{12g}$, and $X^{12h}$ are independently H or an optionally substituted $C_1$-$C_6$ alkyl, or $X^{11a}$ and $X^{12a}$, $X^{11b}$ and $X^{12b}$, $X^{11c}$ and $X^{12c}$, $X^{11d}$ and $X^{12d}$, $X^{11e}$ and $X^{12e}$, $X^{11f}$ and $X^{12f}$, $X^{11g}$ and $X^{12g}$, and, $X^{11h}$ and $X^{12h}$ each may be taken together with a carbon atom to which they are both bonded to form a C3-C6 cycloalkane ring or a 3- to 6- membered heterocycloalkine ring;

$X^{13c}$ and $X^{13e}$ are independently H or an optionally substituted $C_1$-$C_6$ alkyl;

R, $R^{2b}$, $R^{2f}$, $R^{2g}$ and $R^{2i}$ are independently i) H, ii) an optionally substituted $C_1$-$C_{18}$ alkyl, iii) an optionally substituted $C_2$-$C_{18}$ alkenyl, iv) an optionally substituted $C_2$-$C_{18}$ alkynyl, v) an optionally substituted 3-to 15-membered hydrocarbon ring group, or vi) an optionally substituted 3-to 15-membered heterocyclic ring group, or a salt thereof.

* * * * *